United States Patent [19]

Elsner et al.

[11] 4,158,309
[45] Jun. 19, 1979

[54] VARIABLE MOUNTING ASSEMBLY FOR TRANSDUCERS EMPLOYED IN NUCLEAR REACTOR VESSEL INSPECTION APPARATUS

[75] Inventors: Hans J. Elsner, Pittsburgh; Ronald F. Antol, N. Huntingdon; Raymond P. Castner, Monroeville, all of Pa.

[73] Assignee: Westinghouse Electric Corp., Pittsburgh, Pa.

[21] Appl. No.: 781,380

[22] Filed: Mar. 25, 1977

[51] Int. Cl.² .......................................... G01N 29/04
[52] U.S. Cl. ....................................... 73/641; 73/623; 176/19 R
[58] Field of Search .................. 340/85, 284; 248/200, 248/184; 176/19 R; 73/618, 619, 620, 622, 623, 625, 633, 640, 641

[56] References Cited

U.S. PATENT DOCUMENTS

| | | | |
|---|---|---|---|
| 2,605,072 | 7/1952 | Klein et al. | 248/184 |
| 3,056,286 | 10/1962 | Gibson et al. | 73/622 |
| 3,170,114 | 1/1965 | Placke | 248/284 |
| 3,183,709 | 5/1965 | Rankin et al. | 73/622 |
| 3,289,468 | 12/1966 | Vander Veer et al. | 73/641 |
| 3,552,190 | 1/1971 | Lefebvre | 73/622 |
| 3,712,119 | 1/1973 | Cross et al. | 73/625 |
| 3,721,118 | 3/1973 | Jeffras | 73/633 |
| 3,837,202 | 9/1974 | Hetherington et al. | 73/641 |
| 3,895,685 | 7/1975 | Gillette et al. | 73/625 |
| 4,055,988 | 10/1977 | Dutton, Jr. | 73/620 |

*Primary Examiner*—Samuel W. Engle
*Assistant Examiner*—S. A. Cangialosi
*Attorney, Agent, or Firm*—L. A. DePaul; Z. L. Dermer

[57] ABSTRACT

A positionally variable mounting assembly for transducers used to interrogate a nuclear reactor vessel is disclosed. Means are provided for clamping each transducer of an array about its flange in a central restraining block. The central restraining block is, in turn, pivotally mounted in a yoke.

The yoke is movable secured to bars or rails bolted to the transducer plate and, by loosening appropriate bolts, can be moved along the ways or pivoted about one of them. Further, the restraining block can be removed from the yoke and pivotally clamped in a different orientation to upstanding brackets attached to the transducer array plate, or rotated through 90° and then secured again in the yoke.

2 Claims, 33 Drawing Figures

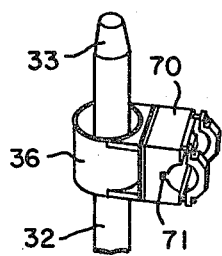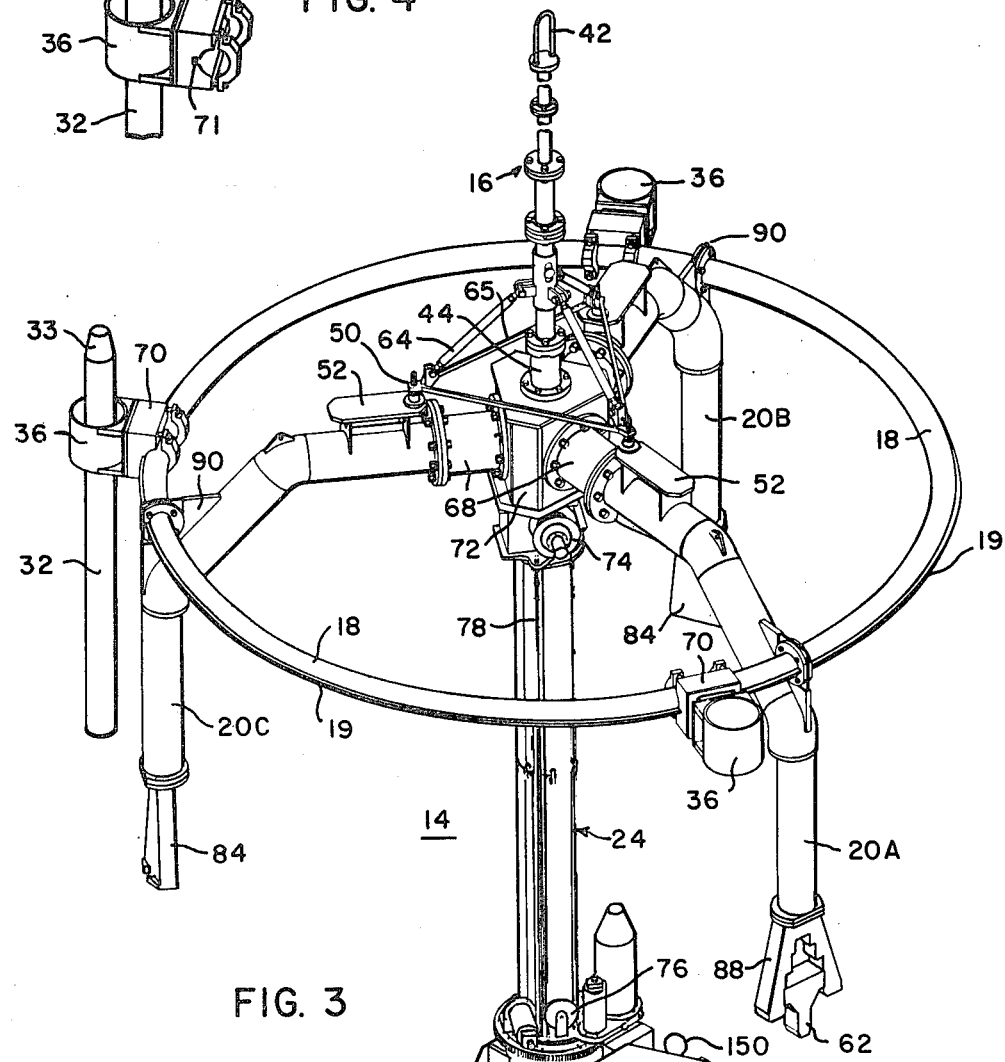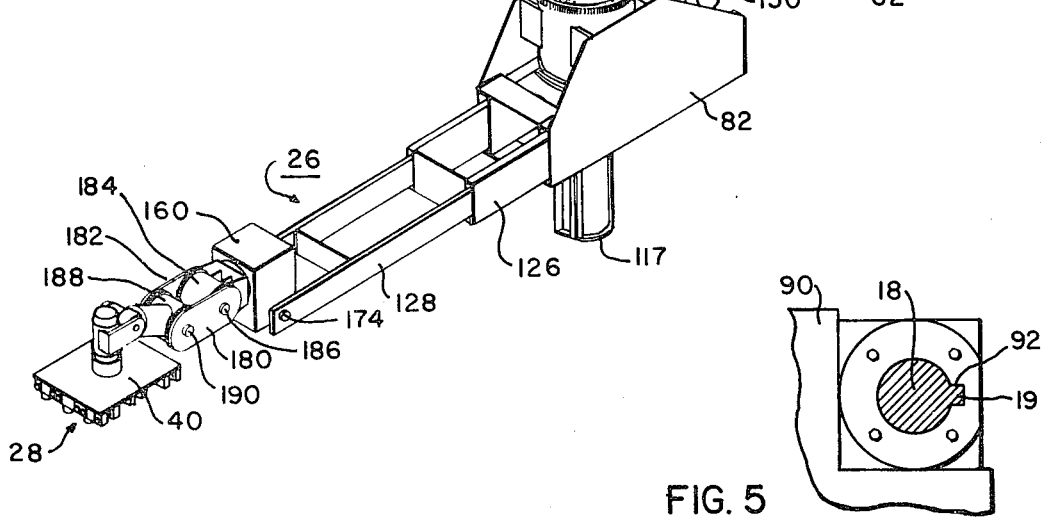

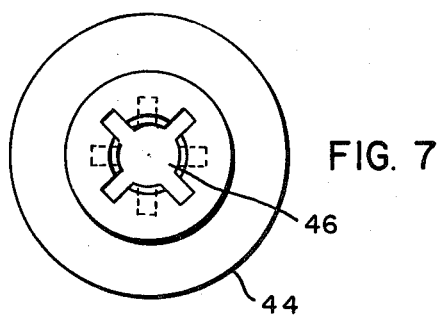
FIG. 7
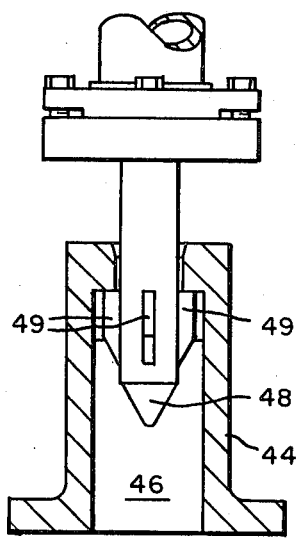
FIG. 8
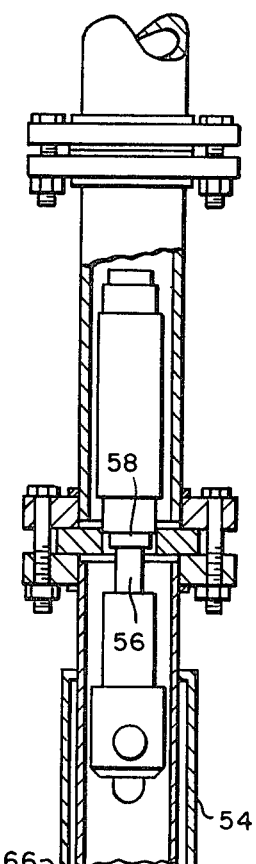
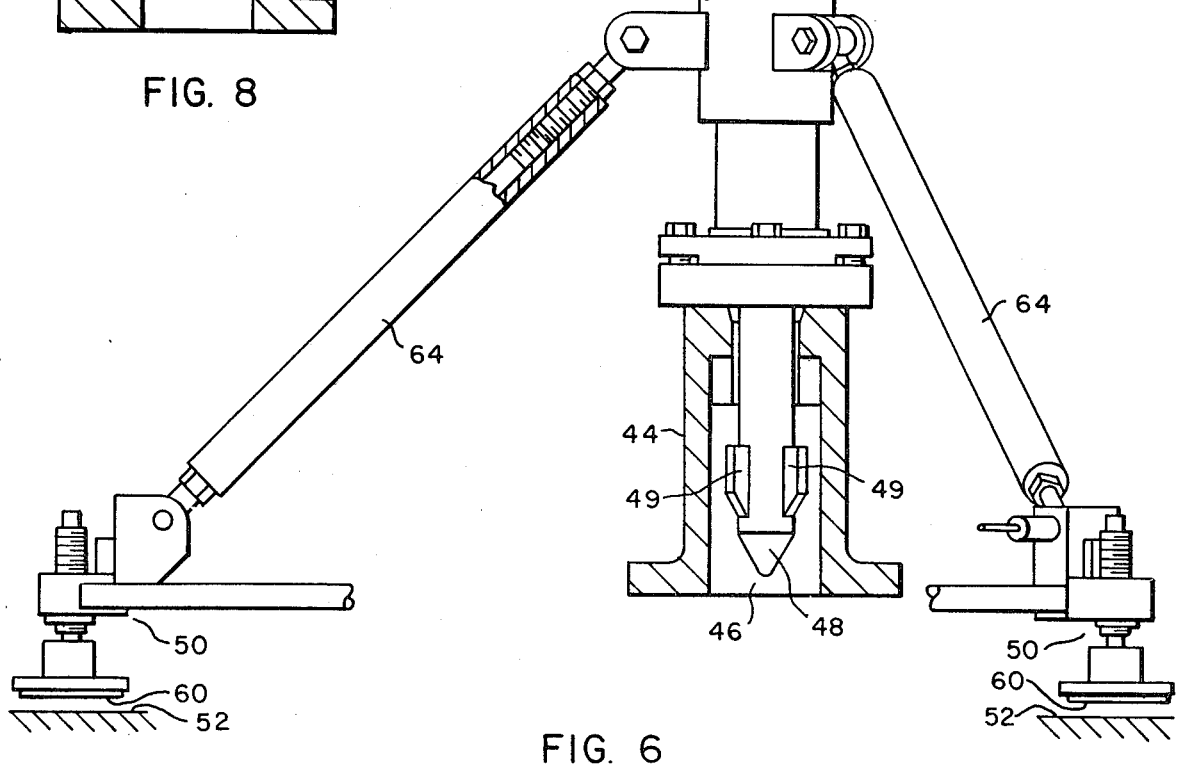
FIG. 6

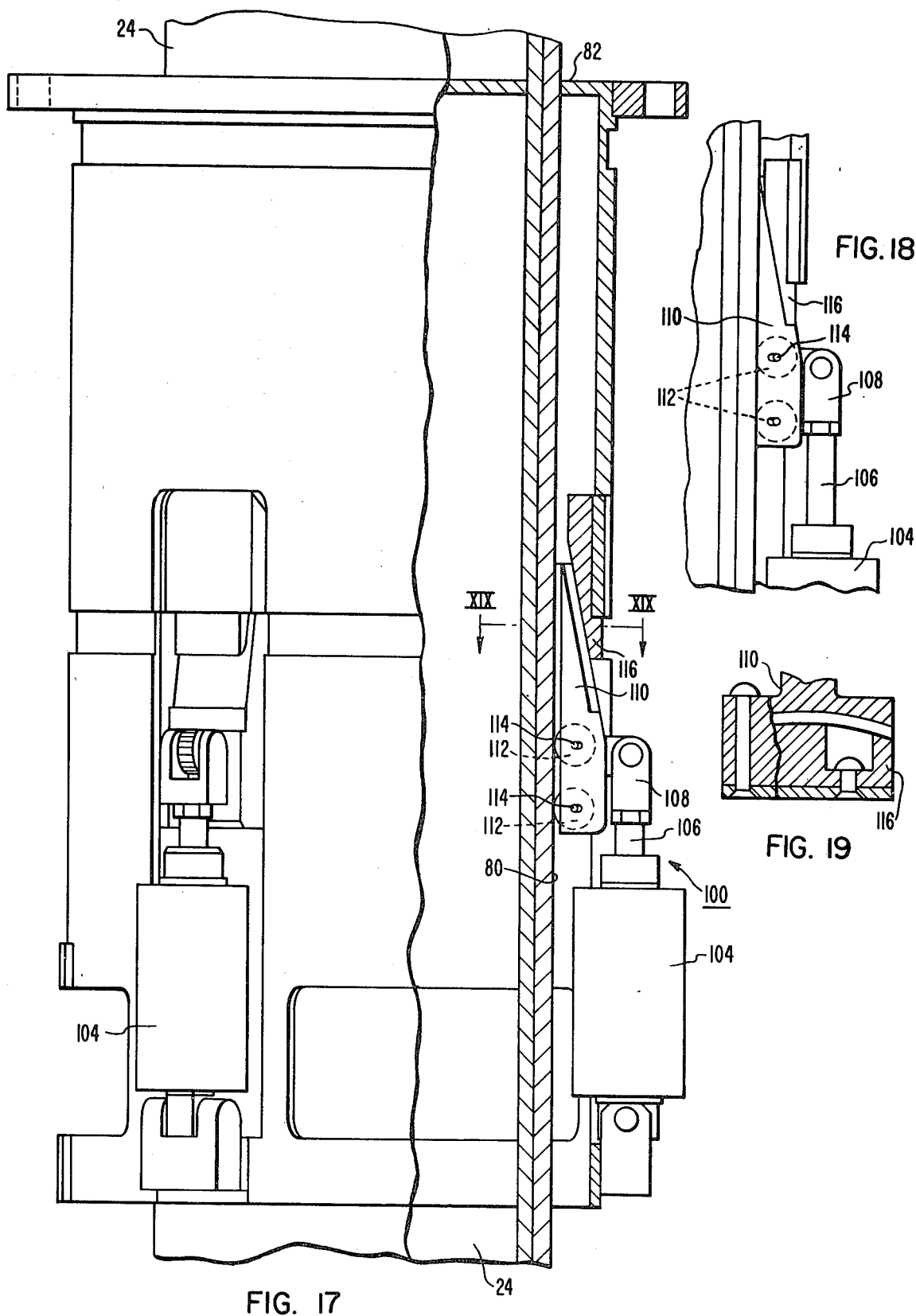

VARIABLE MOUNTING ASSEMBLY FOR TRANSDUCERS EMPLOYED IN NUCLEAR REACTOR VESSEL INSPECTION APPARATUS

CROSS-REFERENCE TO RELATED APPLICATIONS

This application is hereby cross-referenced to the following patent applications which were commonly filed herewith and which are commonly assigned:

U.S. Patent Application Ser. No. 781,403, filed Mar. 25, 1977 entitled "Positioning Means For Circumferentially Locating Inspection Apparatus In A Nuclear Reactor Vessel", filed in the name of David C. Burns;

U.S. Patent Application Ser. No. 781,381, filed Mar. 25, 1977 entitled "Segmented Articulating Manipulator Arm For Nuclear Reactor Vessel Inspection Apparatus", filed in the names of David C. Burns and Lanson Y. Shum;

U.S. Patent Application Ser. No. 781,390, filed Mar. 25, 1977 entitled "Pulley System Including Emergency Locking Means For Nuclear Reactor Vessel Inspection Apparatus", filed in the name of Renato D. Reyes;

U.S. Patent Application Ser. No. 781,401, filed Mar. 25, 1977 entitled "Emergency Braking System For Nuclear Reactor Vessel Inspection Apparatus", filed in the name of Renato D. Reys;

U.S. Patent Application Ser. No. 781,396, filed Mar. 25, 1977 entitled "Emergency Disconnect Means For The Manipulator Arm Of A Nuclear Reactor Vessel Inspection Apparatus", filed in the names of Arthur F. Jacobs and Duane W. Morris;

U.S. Patent Application Ser. No. 781,404, filed Mar. 25, 1977 entitled "Pressurized Cabling And Junction Boxes For Nuclear Reactor Vessel Inspection Apparatus", filed in the names of Charles V. Fields and Raymond P. Castner; and U.S. Patent Application Ser. No. 781,402, filed Mar. 25, 1977 entitled "Emergency Retraction Means For The Manipulator Arm Of A Nuclear Reactor Vessel Inspection Apparatus", filed in the names of Arthur F. Jacobs and Duane W. Morris.

BACKGROUND OF THE INVENTION

Nuclear reactor vessels employed in the commercial generation of electrical power are of two types; the pressurized water type or the boiling water type. In either case, the reactor vessel utilizes a generally cylindrical metallic container having a base and a top flange welded thereto. The main cylinder portion itself usually comprises a series of lesser cylinders welded to each other. In addition, a plurality of circumferentially spaced nozzles extend through the main cylinder wall and are welded thereto. Thus, numerous welds are necessarily used in fabricating the reactor vessel, in mating the top flange to the main cylindrical body and in securing the inlet and outlet nozzles to the reactor vessel wall.

The reactor vessel, in use, is encased in a thick concrete containment area. However, the structural integrity of the reactor vessel, the concrete containment notwithstanding, due to the operating environment is of critical importance.

The weld areas of the reactor vessel are, of course, inspected prior to its initial use. Such inspection is carried out with all portions of the vessel relatively accessible to an inspection device prior to its encasement in the concrete containment. However, in-service inspection of the reactor vessel welds is not only desirable, but is mandated under governmental regulations.

Under such regulations, it is required that the vessel weld areas be subjected to periodic volumetric examination whereby the structural integrity of the vessel is monitored. Due to the nature of an in-service inspection, the device designed to accomplish the specific weld examinations must be capable of successfully operating in an underwater and radioactive environment under remote control while maintaining a high degree of control over the placement and movement of the inspection sensors.

The operating constraints are further complicated by the variety of reactor vessel sizes to which the inspection device must be able to be accommodated. Furthermore, the inspection device must not only be compatible with the weld placements of the reactor vessels now in use, but must also be sufficiently versatile to adapt to inspection duty in future vessels. In addition, the inspection device must be arranged in its use to have only minimal impact with normal refueling and maintenance operations.

The use of ultrasonic transducers to inspect metal welds is known. One such system is described in the periodical *Materials Evaluation*, July 1970, Volume 28, No. 7, at pages 162–167. This article describes a transmitter-receiver type ultrasonic inspection system for use in the in-service inspection of nuclear reactor vessels. The positioning arrangement for the transducers uses a track which is mounted on the interior wall of the reactor vessel.

A method and apparatus for ultrasonic inspection of a pipe from within is disclosed in U.S. Pat. No. 3,584,504. In the apparatus disclosed therein, a transducer array is mounted on a carrier which is rotatable, by means of a central shaft of the apparatus, within the pipe.

In U.S. Pat. No. 3,809,607, a nuclear reactor vessel in-service inspection device is detailed, which device is adapted to permit remotely controlled and accurate positioning of a transducer array within a reactor vessel. This device comprises a positioning and support assembly consisting of a central body portion from which a plurality of radially directed support arms extend. The ends of the support arms are extended to and adapted for being seated on a predetermined portion of the reactor vessel to define a positional frame of reference for the inspection device relative to the reactor vessel itself. Repositioning and support assemblies are provided and include integral adjustment means which cooperate to permit the simultaneous variation of the extension of the support arms thereby allowing the inspection device to fit reactor vessels of differing diameters. A central column is connected to the positioning and support assemblies, which central column extends along the longitudinal axis thereof. One or more movable inspection assemblies are connected to the central column and include drive and position indicating means. Three specific inspection subassemblies include a flange scanner, a nozzle scanner and a vessel scanner. Each of these scanners employ multiprobe transmitter-receiver ultrasonic transducers to permit more accurate volumetric plotting of the integrity of the welds used in fabricating the reactor vessel.

Since the development of the above-identified inspection devices, the original inspection code has been amended to call for more reliable and more rigorous inspections. In addition, these prior art devices were unable to accurately measure or reach certain weld areas of the reactor vessel. Still other drawbacks in the prior art inspection devices were the reliability and speed of the actual inspection effort.

One particular problem which was not entirely solved by the above-described prior art devices was that of mounting the transducers, particularly where only a single array was to be used. Any mounting assembly used for securing a particular transducer to a single array plate would, of necessity, have to be positionally variable in order to accommodate the many orientations required during inspection. If such were not the case, the array or the entire inspection device would have to be withdrawn from the vessel to effect changes which would obviously slow down the inspection effort considerably.

SUMMARY OF THE INVENTION

Accordingly, there is provided a highly versatile and positionally variable transducer mounting assembly. A restraining block and locking means therefore are utilized to removably and rotatably restrain a transducer therein. The restraining block is pivotally secured to a yoke which girdles it by first connecting means which are removable for use with just the restraining block alone.

The yoke and restraining block are movably secured, in turn, to guide means by second connecting means which permit the yoke to be slid along the guide means or pivoted independently with respect to the guide means. The guide means are bolted to the transducer array plate. The second connecting means are further adapted to permit the yoke to be secured thereto in differing orientations. The guide means comprise two rails or bars which are secured respectively to opposite sides of the yoke by the second connecting means. When appropriately adjusted, the second connecting means permits the yoke to be moved along the bars or pivoted about one of the bars while being moved away from the other. Either action can be performed independently of the other.

BRIEF DESCRIPTION OF THE DRAWINGS

The following is a brief description of each of the drawing figures used herein to describe the invention:

FIG. 3 is an isometric view of the inspection apparatus;

FIG. 4 shows an isometric view of a bushing and clamp used to secure portions of the inspection apparatus shown in FIG. 3;

FIG. 5 shows a plan view, partly in section, of a mounting bracket used to secure portions of the inspection apparatus shown in FIG. 3;

FIGS. 6, 7 and 8 are plan views, partly in section, of a lifting assembly employed to align, seat and remove the inspection apparatus shown in FIG. 3;

FIG. 17 is a plan view, partly cut away, illustrating an emergency braking system in its rest position;

FIG. 18 is a plan view of the emergency braking system shown in FIG. 17 in its fully braked position;

FIG. 19 shows a partial cross-sectional view of the emergency braking system depicted in FIG. 17;

DESCRIPTION OF THE PREFERRED EMBODIMENT

Figure 1:
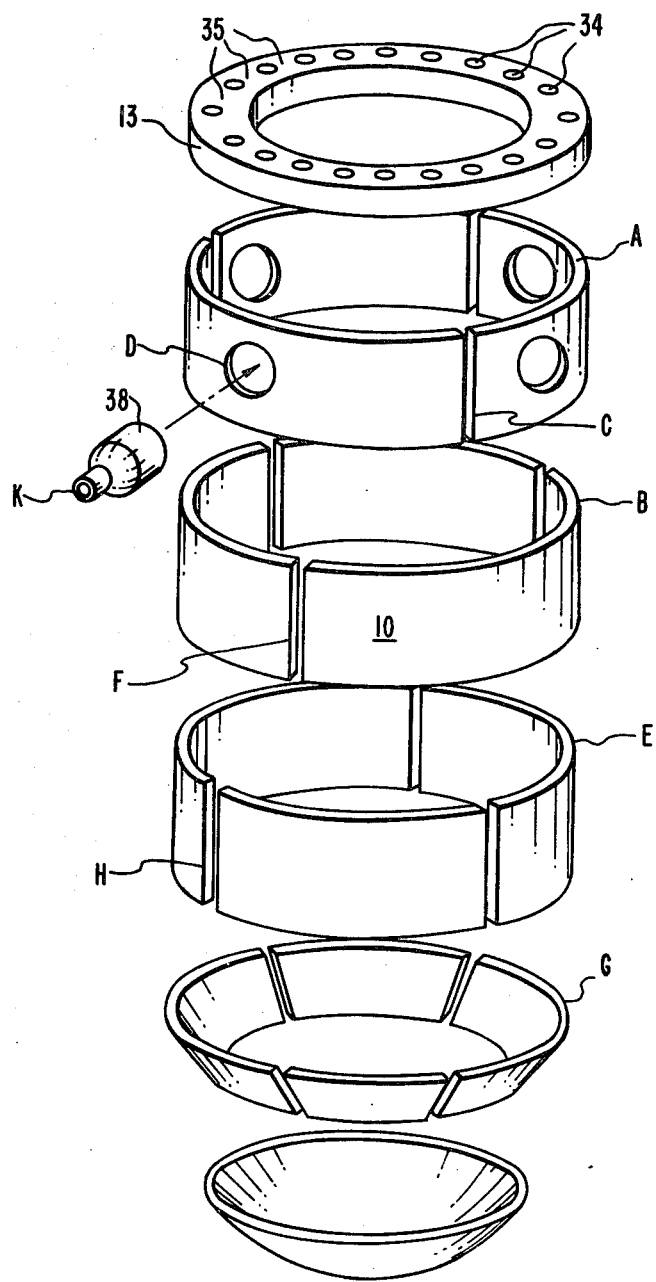
FIG. 1 shows an exploded view of a nuclear reactor vessel and the several welds made in the fabrication thereof.

Referring now to the drawings wherein identical reference numerals have been used in the several views to identify like elements, FIG. 1 shows an exploded view of a nuclear reactor vessel 10. While the vessel 10 may be fabricated in differing ways, the overall cylinder which results from welding together the several smaller cylinders 12 is used herein as an illustrative example for purposes of this description. The several welds, A–K, shown in FIG. 1 are typically those which are to be inspected together with the stud holes 34 and the ligament areas 35 therebetween of the vessel top flange 13. It will be understood by those familiar with the inspection code requirements for nuclear reactor vessels, that not all of the welds A–K or the top flange 13 are necessarily inspected at the end of one time period, but that any inspection apparatus therefor must be capable of efficiently and accurately determining the integrity of the vessel welds A–K and its top flange 13, at one time or in predetermined code specified groupings. Further, the inspection apparatus must be accurately positioned to accomplish vessel interrogation without harming the top flange 13 and, in particular, its ability to form a proper seal with the vessel header (not shown).

Figure 2:
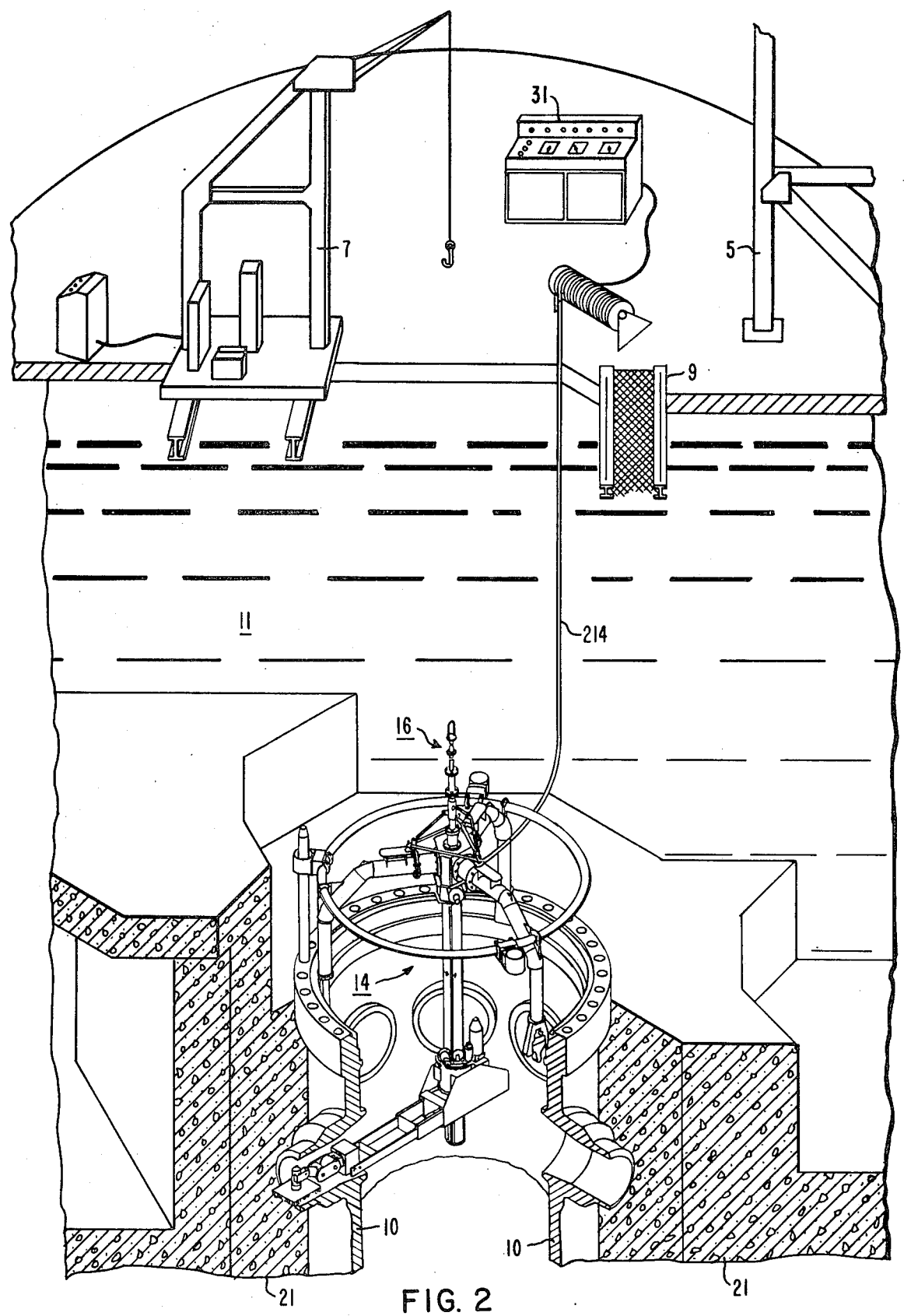
FIG. 2 illustrates a representative view of an inspection site with the inspection apparatus seated in the reactor vessel.

FIG. 2 depicts an illustrative example of an inspection site. The inspection apparatus 14 is shown therein seated in the reactor vessel 10. Prior to inspection, the apparatus 14 is assembled using an erection rig 5 partially shown. After assembly, the inspection apparatus 14 is lowered by the site work crane 7 into the reactor vessel pool 11 and into the vessel 10. The work bridge 9, also partially shown in FIG. 2, can be utilized as necessary.

The inspection apparatus 14 is illustrated in FIG. 3. It comprises a quick-disconnect lifting assembly 16, a support ring 18 having an annular key 19 attached thereto, three support legs 20A, 20B and 20C, a head support assembly 22, a main column 24, a manipulator arm 26, a transducer array 28 and an overall control system 30 which includes an assortment of motors, resolvers and cabling, and is mainly resident in a console 31. These main elements cooperate, in a manner to be more specifically described hereinafter, to permit inspection of the reactor vessel 10 in accordance with code requirements.

Figure 9:
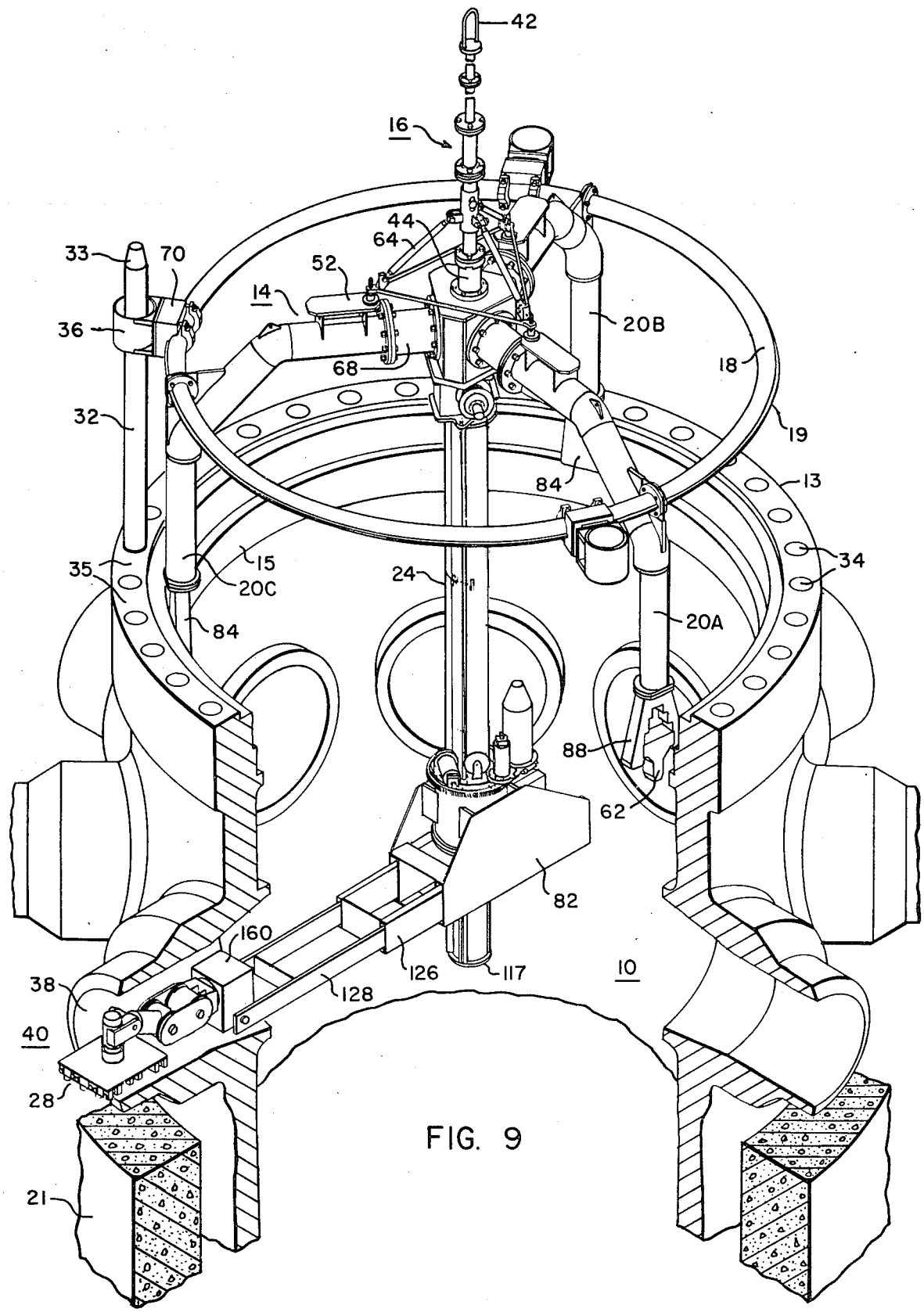
FIGS. 9 and 10 are isometric views of the inspection apparatus showing the manipulator arm thereof in two of its possible inspection positions.
Figure 10:
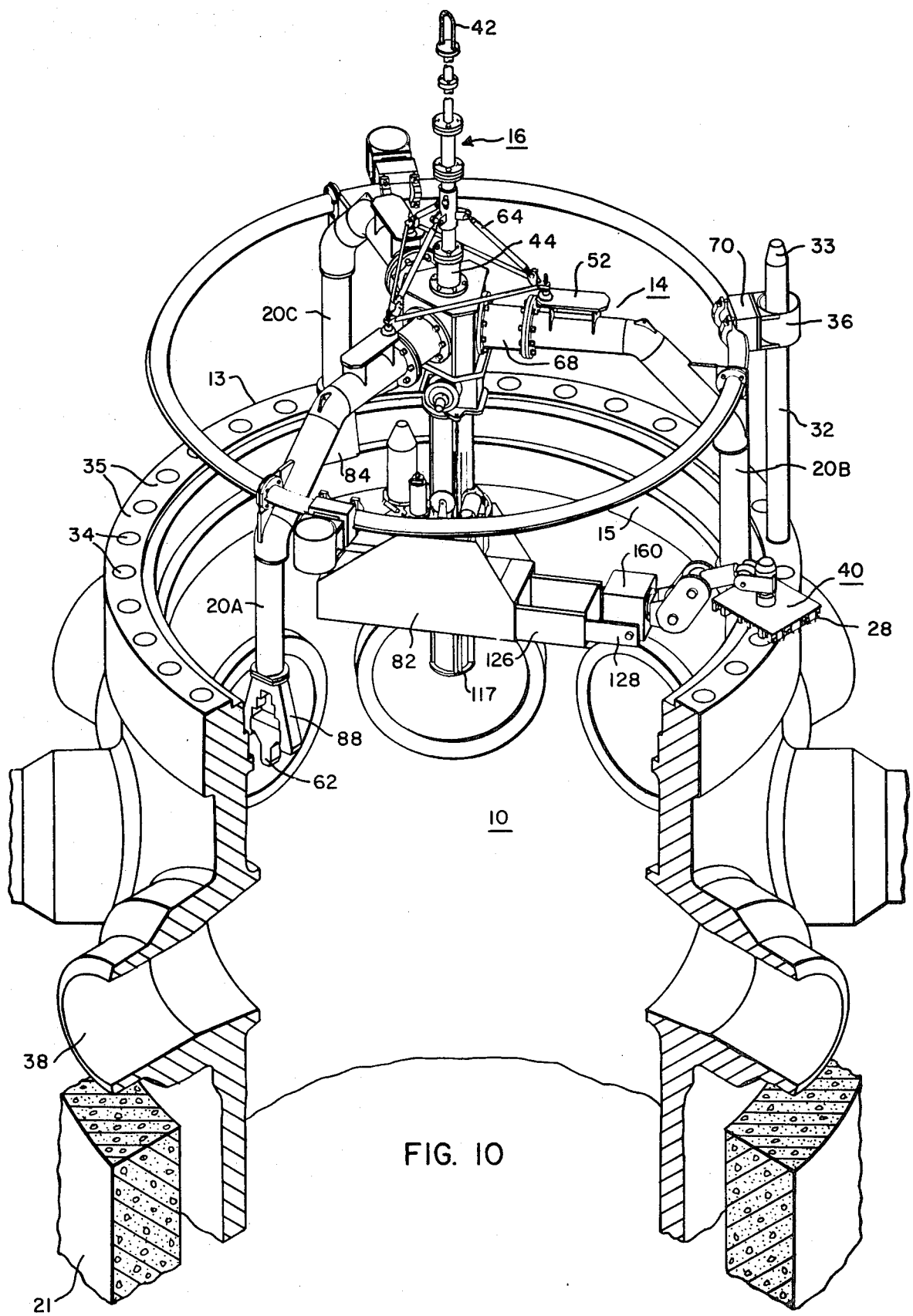

The inspection apparatus 14 is adapted to be lowered into the reactor vessel 10 and is shown in two of its many possible inspection positions in FIGS. 9 and 10. Prior to insertion of the inspection apparatus 14, the reactor vessel header is removed and tapered guide studs 32, having chamfered heads 33, are inserted into three of the stud holes 34 which have been designated for that purpose. With the guide studs 32 in place, the inspection apparatus 14 is fully lowered into the reactor vessel 10 and positively seated therewithin, as shall be hereinafter explained. The guide studs 32 are engaged by guide stud bushings 36 which are movably mounted to the support ring 18. Accurate circumferential positioning of the inspection apparatus 14 is accomplished through the employment of the guide studs 32 and guide bushings 36 in conjunction with a specially adapted support leg show 88, to be more fully described below.

The clearance between the guide stud bushings 36 and the guide studs 32 is typically a maximum of only $\frac{3}{8}$". Therefore, it is of critical importance that the inspection apparatus 14 be lowered into the reactor vessel 12 with the guide studs 32 and bushings 36 in near perfect alignment with each other. Alternatively stated, the inspection apparatus 14, which is a relatively heavy piece of equipment, must be closely aligned with respect to the vertical and horizonal axis or the guide bushings 36 will be cocked with respect to the guide studs 32 causing the inspection apparatus 14 to hang up thereon, which might result in damage to the inspection apparatus 14, the guide studs 32 or the reactor vessel 10. Thus, the lifting assembly 16 must be adjustable to accommodate the cantilevered weighting effect of manipulator arm 26 and/or any weight distribution disparity in the inspection apparatus 14 which would cause it to tilt from a level attitute as it is being lowered. In addition, with the inspection apparatus 14 in place, the lifting assembly 16 must be quickly and readily removable to allow use of the inspection site work bridge 9 should that be necessary.

The lifting assembly 16 is shown in greater detail in FIGS. 6, 7 and 8. When secured to the inspection apparatus 14, it is engaged by the site crane 7 which connects to the "U" bolt assembly 42 coupled to its uppermost portion. The "U" bolt assembly 42 is shown in FIG. 3. A cylindrical collar 44 having a stepped, star-shaped or cloverleaf bore 46 is bolted to the top of the head support assembly 22. The crane 7 now lowers the lifting assembly 16 until a spider 48 enters bore 46, as shown in FIG. 6. The lifting assembly is then manually rotated about 45°, so that the splines of spider 48 are positioned to engage the hidden or dotted line portion of bore 46 as is shown in FIG. 7. The crane 7 now raises the lifting assembly 16 until the spider 48 abuts the upper surface of the stepped portion of bore 46 at which point it is engaged by and in the collar 44, as is shown in FIG. 8.

At this point in the procedure of connecting the lifting assembly 16 to the inspection apparatus 14, the feet 60 of the ball and socket assemblies 50 are held about 3/16" above the leveling pads 52. The leveling pads 52, as shown in FIG. 3, are connected to the upper portions of the support legs 20. A hydraulic cylinder 54 is now actuated, causing its internal piston 56 to push against a fixed surface 58 forcing the socket feet 60 into tight engagement with the leveling pads 52. Three nonadjustable base struts 65 are utilized to enhance the structural rigidity of the lifting assembly 16 and are connected between the three ball and socket assemblies 50, as is shown in FIG. 3. As connected, the base struts form a triangle, the center of which is coincidental with the central axis of the lifting assembly 16 and the main column 24.

The inspection apparatus 14 is thereby fully secured to the lifting assembly 16 and is now suspended from the crane 7 for alignment procedures prior to being seated in the reactor vessel 10. Such alignment procedures are necessary due to probable repositioning of the movable guide stud bushings 36 from site-to-site to accommodate differing locations of the guide studs 32. In addition, the position and extension of manipulator arm 26 may be different from an inspection start at one site than at another. Further, the vessel locating key 62, shown in FIGS. 3 and 14, may or may not be in use. Consequently, the net effect of these and other possible causes will be to present the inspection team with a different weight distribution at each inspection site, thereby necessitating the alignment procedure. Finally, even if the same weight distribution was expected, proper inspection technique would demand alignment verification.

The alignment procedure is carried out by turning one or more of the turnbuckle struts 64 which are rotatably adjustable and fixedly connected between the three ball and socket assemblies 50 and the slidable sleeve 66 of the hydraulic cylinder 54. Adjustment of the turnbuckle struts 64 has the effect of gimbaling the inspection apparatus 14 about the center axis of the triangle formed by the base struts 65 or the lower end of the lifting assembly 16. This enables the inspection team to plumb the main column 24 of the inspection apparatus 14 and verify its vertical alignment. In addition, each of the three ball and socket assemblies 50 can be individually adjusted to shift the position of the end of the turnbuckle strut 64 connected thereto to effect adjustment of the inspection apparatus 14 with respect to both the vertical and horizontal axes. Horizontal alignment is verified by checking the level on any one of the three leveling pads 52.

The lifting assembly 16 is capable of being quickly disconnected by reversing the order specified above. First, the hydraulic cylinder 54 is deactivated causing its outer sleeve 66 to move upwards lifting the socket feet 60 from the leveling pads 52. The crane 7 now lowers the lifting assembly 16 by an amount sufficient to allow the spider 48 to fall out of engagement with the upper portion of the bore 46 of collar 44. Spider 48 can now be rotated and withdrawn from collar 44. After this is done, the entire lifting assembly can be removed by the crane 7, freeing it for other work, and leaving the inspection apparatus 14 seated in the reactor vessel 10. Alternatively, the lifting assembly 16 can be so disconnected after it has been used to remove the inspection apparatus 14 from the reactor vessel 10, leaving the inspection apparatus 14 on resting pads (not shown) or on the erection rig 5 preparatory to shipment. By removing the lifting assembly 16 with the inspection apparatus 14 still seated in the reactor vessel 12, the work bridge 9 can be moved across the vessel pool 11 allowing for the performance of other maintenance or inspection procedures or to assist in the vessel inspection itself.

Referring again to FIG. 3, there is shown three support legs 20A, 20B and 20C. Each of these is joined to the head support assembly 22 by a spacer 68 which is of a length appropriate to the diameter of the vessel to be inspected. It should be noted that for differing diameter reactor vessels, the spacers 68 and the support ring 18 are selected and sized so that the guide stud bushings 36 extend radially to a point where they will be aligned with and then engage the guide studs 32. Very small variations in radial dimensions are accommodated by loosening the guide stud bushing clamps 70 and inserting shims of an appropriate thickness which would have the effect of moving the center of the guide stud bushings 36 radially outward of support ring 18 as desired. It should also be noted that the guide stud bushing clamps 70, when loosened, permit movement of the bushings 36 along the support ring 18 to accommodate variations in the placement of the guide studs 32 in the vessel top flange 13 at different inspection sites.

As previously noted, the guide stud bushings 36 are movably connected to the support ring 18 by the bushing clamps 70. As was also previously noted, the support ring 18 carries an annular key 19 about its outer surface. A keyway 71, see FIG. 4, cut in the surface of clamp 70, which mates with support ring 18, accommodates key 19 and aligns the guide stud bushings 70 on support ring 18 with respect to the remainder of the inspection device 14. In addition, support legs 20A, 20B and 20C are connected to support ring 18 respectively by a bracket 90, see FIG. 5, having a keyed hole 92 therethrough. Thus, the bracket 90 engages the key 19 and positively locates and locks the support legs 20A, 20B and 20C to support ring 18 which enhances the structural stability of inspection apparatus 14. The leveling pads 52 are bolted or welded to the upper segments of the support legs 20A, 20B and 20C in horizontal alignment and are utilized in the manner described above.

Figure 11:
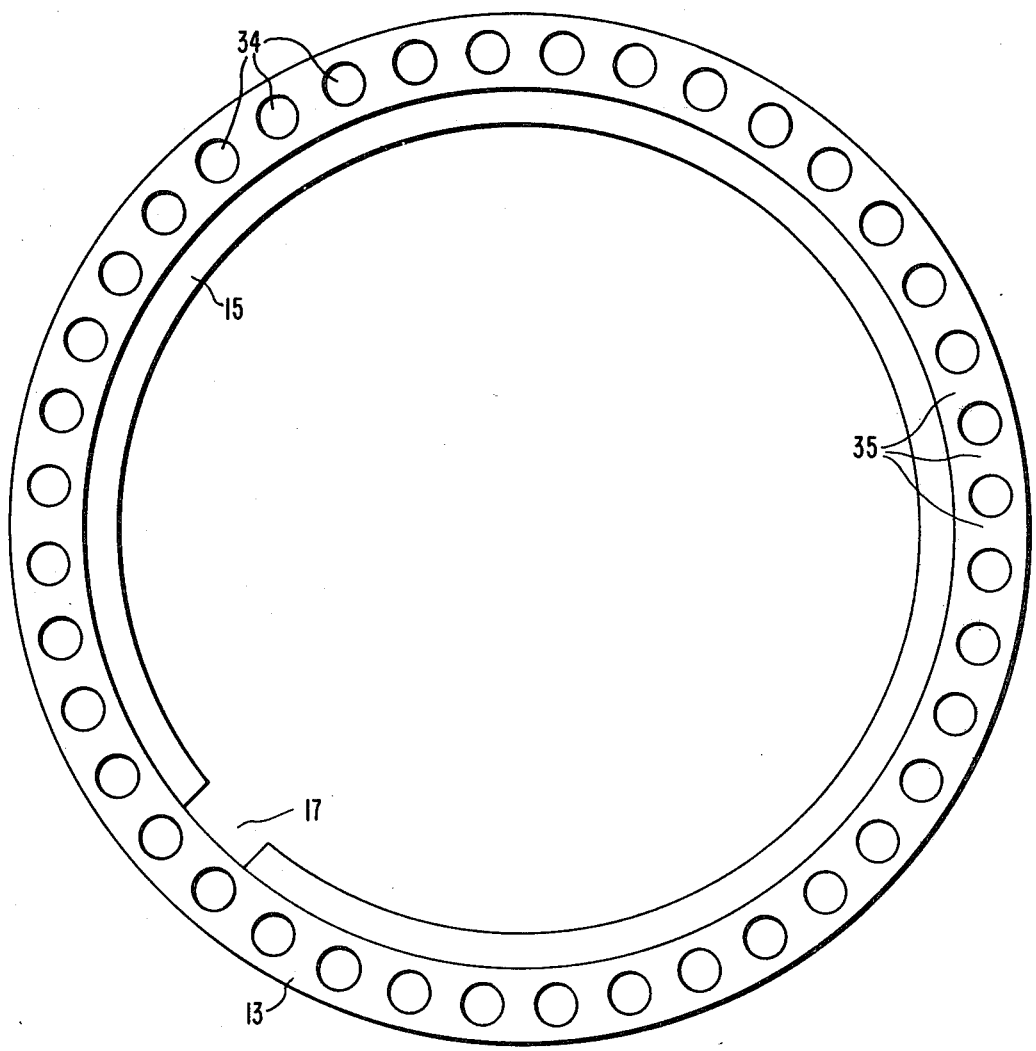
FIG. 11 is a plan view of the reactor vessel's top and circumferential flanges.
Figure 12:
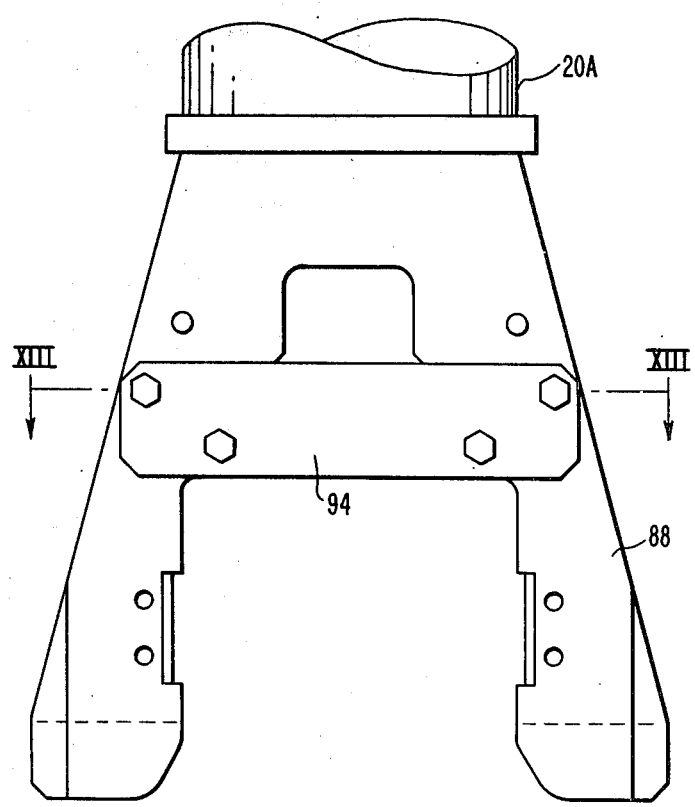
FIG. 12 is a plan view of a specially configured support shoe, utilized to position the inspection apparatus within the reactor vessel, having a keyed plate bolted thereto.
Figure 13:
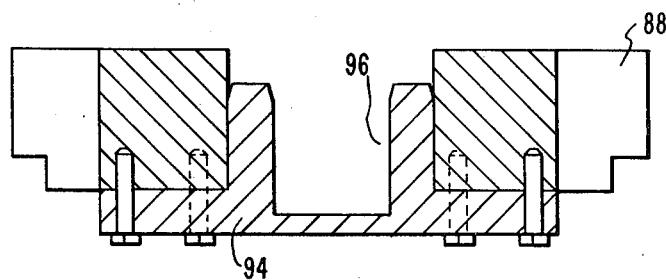
FIG. 13 is a plan view, partly in section, of the shoe and bracket shown in FIG. 12.
Figure 14:
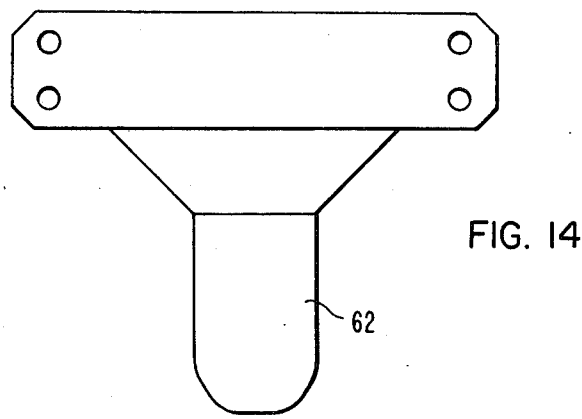
FIG. 14 is a plan view of a locating key used in place of the bracket shown in FIGS. 12 and 13.

When seated within the reactor vessel 10, the three legs 20A, 20B and 20C support the entire weight of the inspection apparatus 14. Stainless steel shoes 84 are bolted respectively to the bottom of support legs 20B and 20C. These shoes rest either on the circumferential vessel flange 15 or on the core barrel flange (not shown), depending on whether the core barrel has been removed. A special "A" shaped shoe 88 is bolted to the end of support leg 20A and is adapted to accurately position inspection apparatus 14 as it is being seated within the reactor vessel 10. With the core barrel remaining in the vessel 12, a plate 94 having a keyway 96 cut therein is bolted to shoe 88 as shown in FIGS. 12 and 13. As it is being seated, keyway 96 engages a head-to-vessel alignment pin, the position of which is known, and positively locates the inspection apparatus 14 within the vessel 10. As mentioned above, the clearance between the guide studs 32 and the guide stud bushings 36 is about ⅜" and their engagement yields a coarse circumferential alignment. The subsequent engagement by keyway 96 of the head-to-vessel alignment pin yields a fine circumferential alignment which provides for an absolutely certain placement of the inspection apparatus 14 within vessel 10. With the core barrel removed for inspection, the plate 94 is removed from shoe 88 and a vessel locating key 62, as shown in FIGS. 3 and 14, is bolted to shoe 88 in its place. The vessel locating key 62 fits into a notch 17 cut in the circumferential vessel flange 15, see FIG. 11, which notch is otherwise covered by the core barrel flange. This engagement of notch 17 by the vessel locating key 62 provides the same fine circumferential alignment means, with the core barrel removed, as was yielded by the use of plate 94. It should be noted that plate 94 can be built up with appropriately configured shims to accommodate the different sized head-to-vessl alignment pins that may be encountered from one vessel to another. Thus, by choice of the shoe 88 configuration, in conjunction with the engagement of the guide studs 32 by the guide stud bushings 36, the exact circumferential location of support leg 20A, and derivatively that of manipulator arm 24, is known and assured. In addition, this positive location or seating of the inspection apparatus is accomplished without touching or threatening the sealing surface of the vessel top flange 13.

Connected immediately below the head assembly 22, as shown in FIG. 3, is a gear box and motor assembly 72 which drives manipulator arm 26 vertically along the main column 24 utilizing a pulley system 75. The main column itself consists of several sections of flanged pipe bolted together. Sections may be readily removed or added to accommodate the depth of reactor vessel inspection requirements. Each section is individually encased so that water cannot enter therein. Between the flanges 85 thereof, the sections of main column 24 carry a track 78 which is used, in conjunction with a sensor to be hereinafter described, to determine the extent of vertical travel or, alternatively stated, to fix the vertical position of manipulator arm 26. The main column sections also include "U" shaped grooves 80 which accommodate bearings carried by manipulator arm 26. The grooves 80 and flanges 85 combine functionally to restrain the manipulator arm 26 from making any unwanted or undesirable rotary movements about the main column 24 as it travels therealong.

Figure 15:
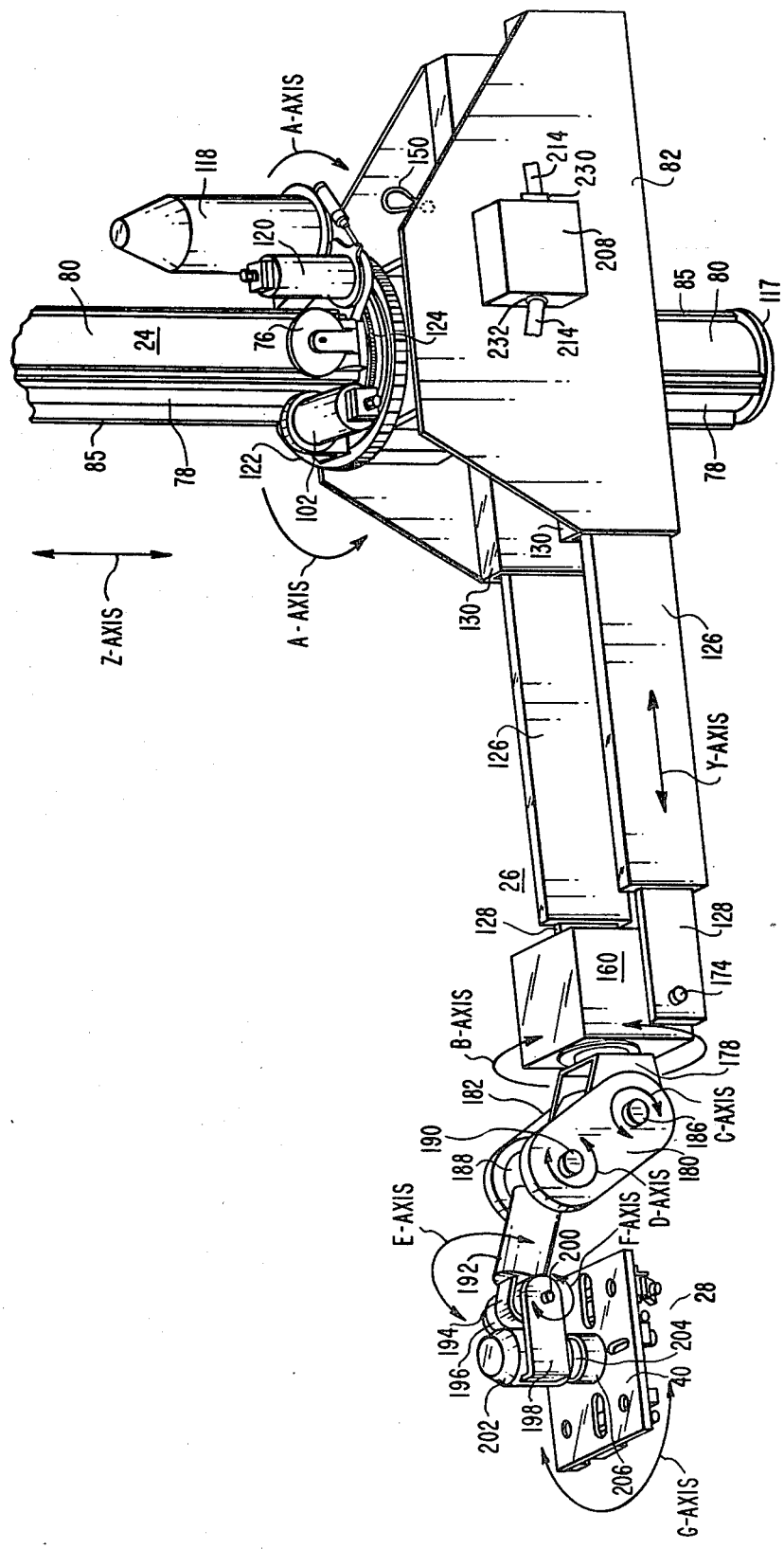
FIG. 15 is an isometric view of the manipulator arm used in the inspection apparatus shown in FIG. 3.
Figure 16:
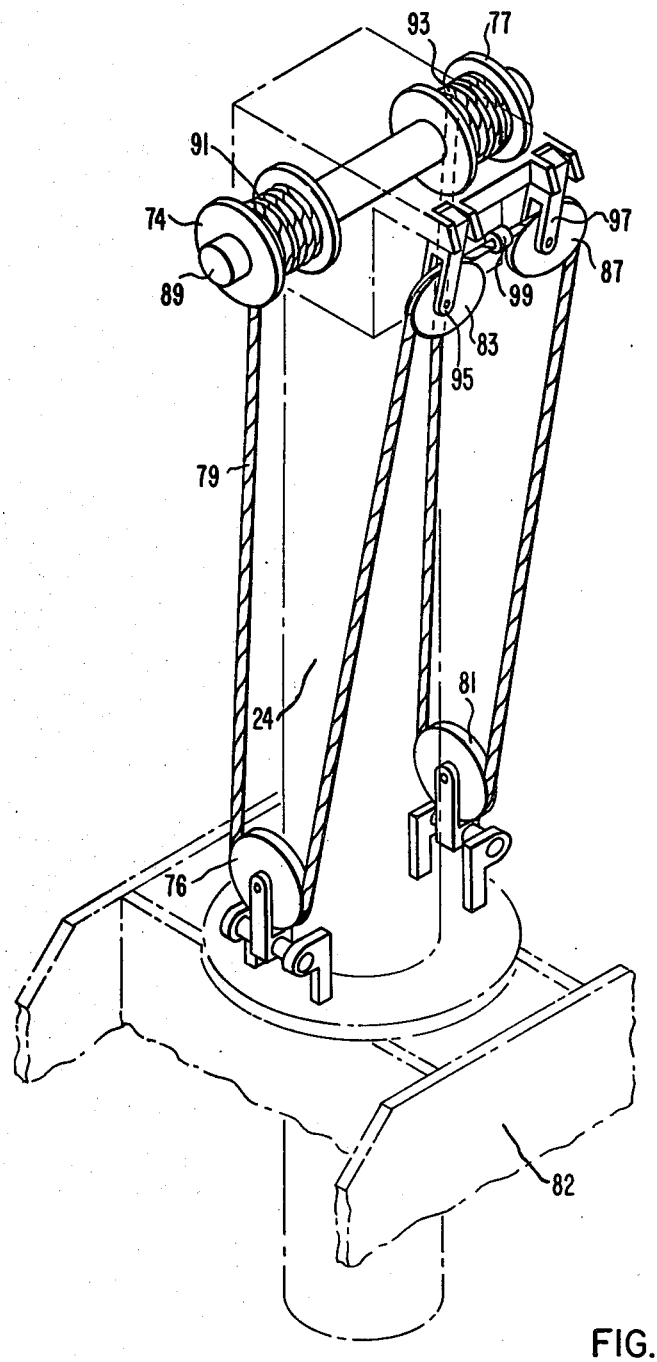
FIG. 16 is a schematic view of a pulley system which is incorporated in one of the drive assemblies for the manipulator arm.
Figure 20:
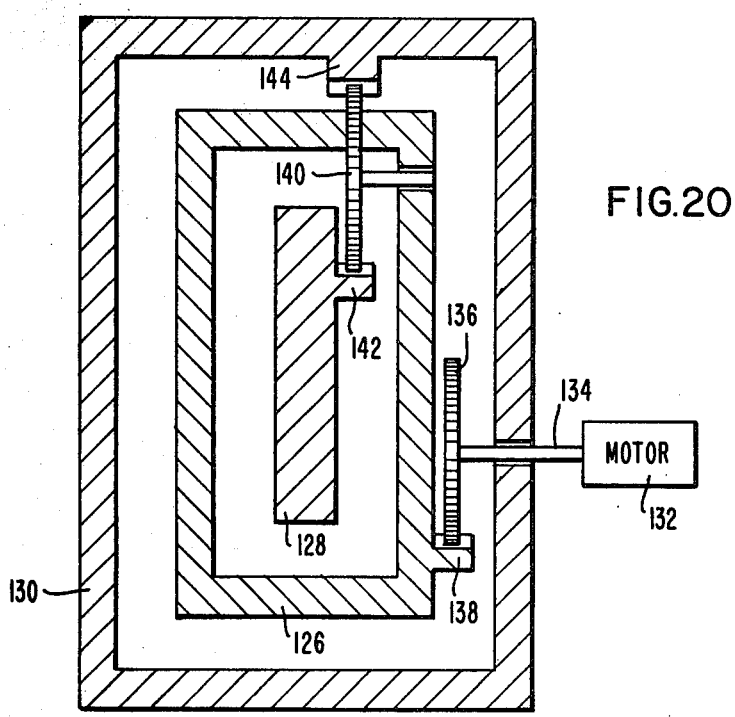
FIG. 20 is an end view representation of a telescoping drive assembly used, in part, to position the manipulator arm.

The manipulator arm 26, which is more clearly shown in FIG. 15, includes a carriage assembly 82 which rides on the main column 24 in the "U" shaped grooves 80. The carriage assembly 82 and the remainder of manipulator arm 26 would typically be fabricated from a low weight material which can withstand the hostile operating environment. The carriage assembly 82 is fitted with internally mounted and sealed ball bearings which ride in and are engaged by the "U" grooves 80 and facilitate vertical movements by manipulator arm 26 on the main column 24. When the vertical drive motor (not shown) in the vertical motor assembly 72 is actuated, it rotates the drive pulleys 74 and 77 as is shown in FIG. 16. A pulley cable 79 is looped about the carriage idler pulleys 76 and 81 and the head assembly idler pulleys 83 and 87. When the vertical motor shaft 89 is rotated counterclockwise, the pulley cable 79 is released respectively by both drive pulleys 74 and 77 from their take-up spools 91 and 93, lowering the manipulator arm 26 with equal force on both sides of the carriage assembly 82. This equalization of the release force applied to both carriage idler pulleys 76 and 81 insures that the carriage assembly will not be cocked and therefore hang-up or unduly wear its bearings as it travels down the main column 24. Likewise, when the vertical motor drive shaft 89 is rotated clockwise, the When an emergency retraction of the transducer array 28 becomes necessary, a hook (not shown) is lowered into the reactor vessel 10 to engage the cable ring 150. Once engaged, the ring 150 is pulled up, which action frees the detechable clamp 148 from the carriage assembly 82. Upward force is maintained, moving the cable ring 150 from its initial position 152 towards its final position 154. As the cable ring 150 is pulled upwards toward its final position 154, the retraction cable 142 forces the pulley 144 from its initial position 156 to its final position 158. Since the pulley 144 is secured to the outer telescoping arm 126, it forces it back into the carriage channel 130 as it moves towards its final position 158. Simultaneously, the outer telescoping arm 126 causes the inner telescoping arm 128 to be moved inwardly, through manual operation of the Y axis drive described above, thereby forcibly withdrawing the manipulator arm 26 and the transducer array 28 from within a vessel nozzle 38.

Figure 22:
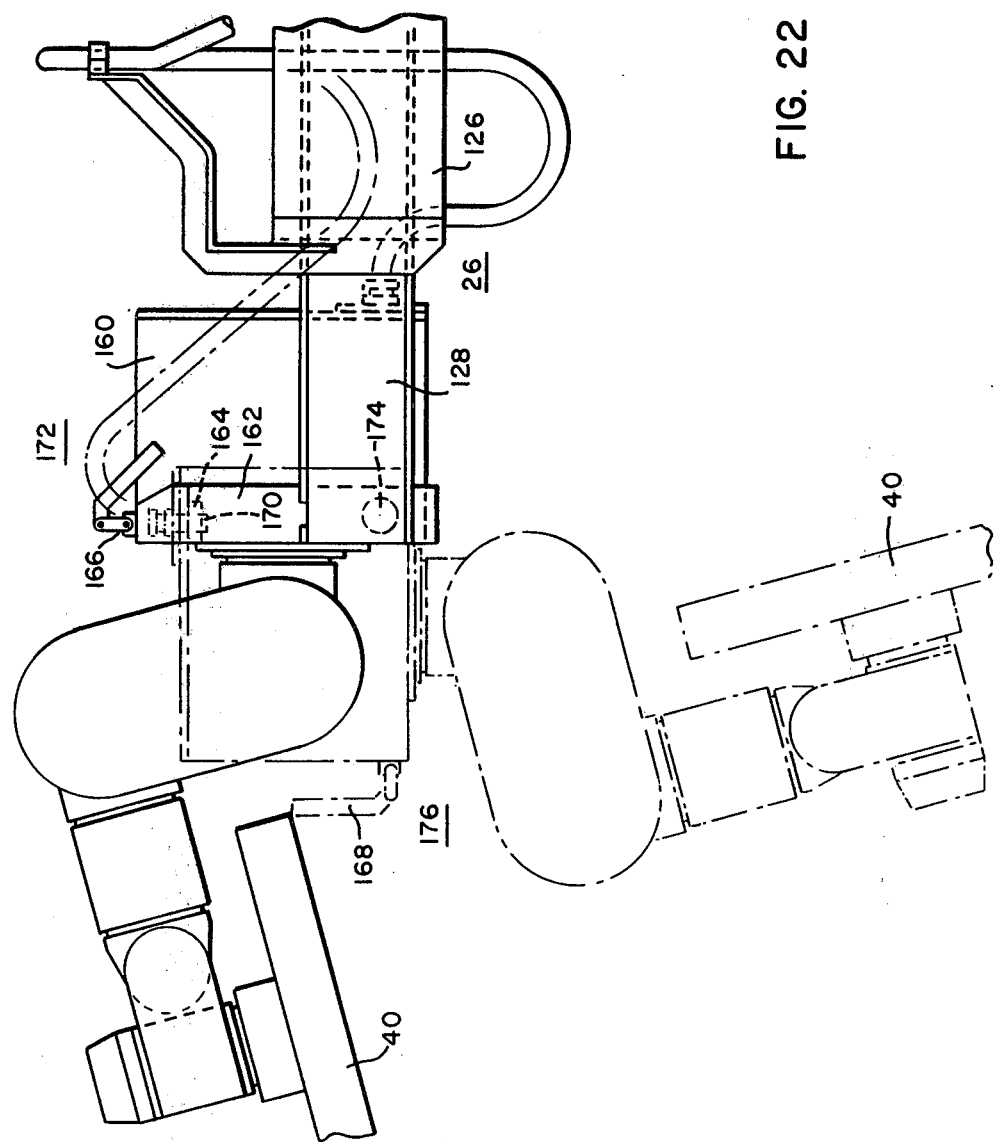
FIG. 22 is an isometric representation of an emergency release system for partially disabling the linkage between segments of the manipulator arm.

B axis motion is obtained by actuating the B axis motor (not shown) which is mounted within the B axis drive housing 160 and connected to mounting bracket 178. As is more clearly illustrated in FIG. 22, the B axis drive housing 160 is secured in the following manner. A mounting bracket 162 is bolted to each of the inner telescoping arms 128. Attached to the upper end portion of bracket 162 is an apertured dog ear 164. Attached to the upper portion of the B axis drive housing 160 is a movable linkage assembly 166 which is actuated by a locked-over-center lever 168. The linkage assembly 166 terminates in a dog 170 which engages the aperture in dog ear 164 when lever 168 is moved to its locked position 172 and holds the B axis drive housing in a normal position with respect to the telescoping arm 128. The bottom portion of the B axis drive housing is movably secured by engagement with a hinge pin 174.

As noted above, the transducer array 28 and manipulator arm 26 can be withdrawn from a vessel nozzle 38 in an emergency situation. However, it may not yet be safe to lift the inspection apparatus 14 from the vessel 10 since the forward portion of the manipulator arm may strike the reactor vessel 10. Accordingly, after the manipulator arm 26 has been manually retracted, the hook is again lowered and engages the linkage lever 168. As the hook and lever 168 are pulled upwardly, the linkage assembly 166 extracts the dog 170 from engagement with the dog ear 164, allowing the B axis drive housing to rotate about hinge pin 174 as is shown in phantom in FIG. 22. With the B axis drive housing in its final position 176, the entire inspection apparatus 14 can be withdrawn from the vessel 10 without any fear of striking the vessel walls.

Further movement of the transducer array 28 is possible along or about five additional axes of movement. In addition to movement of the manipulator arm 26, and derivatively movement of the transducer array 28, along or about the A, B, Y and Z axis, movement can be effected about the C, D, E, F and G axes. The B axis motor shaft is connected to a mounting bracket 178 and, when driven, rotates bracket 178 and all elements connected forwardly thereof about the B axis. Two additional mounting brackets 180 and 182 are secured to the B axis motor bracket 178, as is shown in FIGS. 3 and 15. The C axis motor housing 184 is coupled between and secured to the brackets 180 and 182 with the C axis motor shaft 186 extending through and being drivingly engaged by the brackets 180 and 182. When actuated, the C axis motor drives its shaft 186 and the brackets 180 and 182, as well as all of the manipulator elements connected forwardly thereof, about the shaft 186. Motion in the D axis is achieved in a similar manner. The D axis motor housing 188 is also coupled between and secured to the brackets 180 and 182 with the D axis motor shaft 190 extending through and being drivingly engaged by the brackets 180 and 182. When the D axis motor is actuated to drive its shaft 190, motor shaft 190 and all of the manipulator arm elements connected forwardly thereof are rotated in the D axis. The E axis motor housing 192 is connected to the C axis motor housing 188 with the E axis motor shaft (not shown) being connected to mounting bracket 194. When actuated, the E axis motor shaft drives bracket 194 about the E axis, as well as all of the manipulator arm elements connected forwardly thereof. The F axis motor housing 196 is secured by mounting bracket 194 and by mounting brackets 198. The shaft 200 of the F axis motor (not shown) extends through and drivingly engages the mounting bracket 198. When actuated, the F axis motor drives its shaft 200 and the remainder of the manipulator arm elements connected forwardly thereof through F axis motion. The G axis motor housing 202 is secured to the end of mounting bracket 198. The G axis motor shaft 204 extends outwardly of housing 202 and is clamped into the transducer plate collar 206 which, in turn, is clamped to the transducer array plate 40. When actuated, the G axis motor drives its shaft 204 and the transducer array plate about the G axis. Thus, the transducer array plate 40 and the transducer array 28 mounted thereon, with reference to any point in the reactor vessel 10, can be driven in nine planes of movement or about nine axes of rotation. This highly mobile and segmented articulating drive train can be employed to accurately position the transducer array 28 at any point within the reactor vessel 10.

Figure 23:
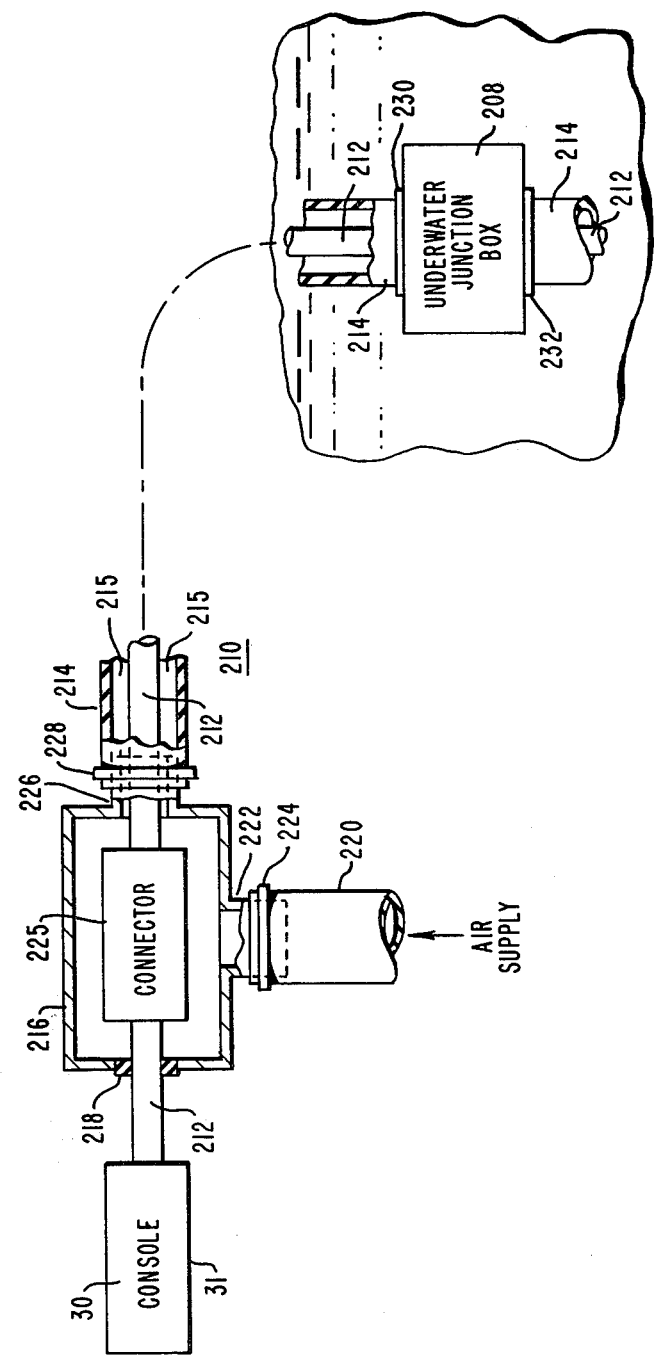
FIG. 23 is a schematic representation of a presurized cabling assembly utilized to connect and energize elements of the inspection apparatus.

Ordinarily, electrical connection to and from the different motors, resolvers and the transducer array 28 would be accomplished by means of components particularly suited for use in an underwater operating environment. To avoid the use of such special components, which are more expensive and require longer delivery times, it was decided to pressurize the electrical cabling system allowing for the use of ordinary components. For example, the junction box 208, shown only in FIGS. 15 and 23 for purposes of clarity, can be pressurized to a degree which would prevent water seepage therein and thusly allow the use of standard electrical connectors. In order to conserve on cabling, the air supply and electrical supply was combined in the cabling assembly 210, shown in FIG. 23. The illustration in FIG. 23 is merely representative of the cabling assembly 210 and only one cable 212 and one dual cable 214 has been shown, although more are used. The electrical cable 212 carries a plurality of electrical conductors to and from the console 31 which would typically include the control system 30. These conductors would be utilized to energize the different motors and transducers and carry signals which would report on transducer and resolver responses, among other things. The cable 212 is routed to the air supply junction box 216 which is sealed at its entry point therewith by a seal 218 to prevent air leakage from junction box 216. An air supply hose 220 is also routed to the air supply junction box 216 and carries air at a pressure significantly higher than atmospheric thereto. The air supply hose 220 is sealingly connected by clamp 224 about an air receiving nozzle 222 extending from the junction box 216.

upward or lifting forces applied to the carriage idler pulleys 76 and 81 is equalized and the carriage assembly 82, as well as the remaining elements of manipulator arm 26, is lifted smoothly, at the proper attitude, up the main column 24. The head assembly idler pulleys 83 and 87 serve to define the upper portion of the pulley cable loop. This upper portion of the cable loop is utilized to equalize any cable slippage or unbalance in the cable 79 which might otherwise unequally tend to pull up on or release idler pulleys 76 and 81. Thus, except for any movement to effect compensation due to an unbalance, the pulley cable 79 is in motion during vertical travel of the manipulator arm 26 only between the drive pulleys 74 and 77 and the carriage idler pulleys 76 and 81 respectively. An emergency cable clip 99 is secured to the cable 79 between the head assembly idler pulleys 83 and 87. If the pulley cable 79 should happen to snap, the clip 99 will become wedged between one of the idler pulleys 83 or 87 and its respective support bracket 95 or 97, thereby restraining further vertical movement of manipulator arm 26.

An emergency braking system 100 is shown in FIGS. 17, 18 and 19. It serves to halt vertical movement of the manipulator arm 26 whenever its vertical speed of travel exceeds a predetermined velocity, typically a speed greater than five inches per second. A vertical velocity rate error signal is developed utilizing a signal generated by the Z axis resolver 102 which engages the vertical track 78 and thereby follows and helps to determine the vertical position and rate of change therein of the manipulator arm 26. When an overspeed condition is sensed by the control system 30, an emergency brake signal is forwarded to three pneumatic cylinders 104 mounted beneath the carriage assembly 82. The pneumatically operated piston 106 of each cylinder 104 is connected via a header 108 to a brake shoe 110. The brake shoe 110 is fitted with spring loaded roller bearings 112 which ride in bearing slots 114 in the brake shoe 110 and are normally urged against the "U" grooves 80 of the main column 24. In the rest position illustrated in FIG. 17, the emergency braking system 100 is disabled and the bearings 112 are spring loaded against the "U" groove 80 holding the brake shoe 110 in its rest position and avoiding unnecessary wear. A cross-sectional view of the brake shoe 100 and brake lining 116 is shown in FIG. 19.

When the emergency brake signal is received by the pneumatic cylinders 104, the pistons 106 thereof are thrust upwardly at a speed significantly in excess of that exhibited by the manipulator arm 26, even in its overspeed condition. This rapid piston movement forces the wedge shaped brake shoe 110 upwardly into contact with the brake lining 116 which is bolted to the bottom of the carriage assembly 82. As the brake shoe 110 fully contacts the positionally fixed brake lining 116, as is shown in FIG. 18, the roller bearings 112 are forced inwardly in slots 114 and the brake shoe 110 becomes jammed against the "U" groove 80 halting further vertical movement of the manipulator arm 26. As noted above, the speed of piston 106 is significantly greater than the overspeed limit of the manipulator arm 26. It is therefore fast enough, when actuated, to overtake the manipulator arm 26 and cause braking action to occur even when the overspeed condition of manipulator arm 26 results from upward movement thereof. Thus, the described emergency braking system 100 functions to halt vertical movement of manipulator arm 26 when an overspeed condition occurs regardless of the direction of vertical or Z axis travel at that time. To insure absolute downward restraint of manipulator arm 26, an emergency stop plate 117, as depicted in FIGS. 3 and 15, is bolted to the bottom section of main column 24. Plate 117 serves to halt downward movement of manipulator arm 26 should the emergency braking system 100 fail to function properly. The manipulator arm 26 is thereby prevented, by either the emergency braking system 100 or the stop plate 117, from striking the bottom of the reactor vessel 10 or any portion thereof as it is vertically driven in the vessel 10.

A axis motion or rotation of the manipulator arm 26 about the main column 24 is shown in FIG. 15. As illustrated therein, actuation of the A axis motor 118 drives the carriage rotary gears 122 and 124 causing the entire manipulator arm to swing about the main column 24. The position of manipulator arm 26 in the A axis is verified by a signal which is generated by the rotary resolver 120. It should be noted with respect to all of the drive motors described herein, whether shown or not, that a resolver or position determining sensor is coupled thereto to provide a signal which is then employed to indicate the position of manipulator arm 26 or any portion thereof, in or about the particular axis of movement associated with the motor being described.

Y axis movement, which is also indicated in FIG. 15, is achieved by driving a set of telescoping arms 126 and 128, which are movable mounted within the carriage channels 130, toward and away from the carriage assembly 82. As is more clearly illustrated in the end view shown in FIG. 17, the Y axis motor 132 is coupled by its shaft 134 to a drive gear 136. When the Y axis motor 132 is actuated, it causes drive gear 136 to be rotated, driving a rack 138 engaged thereby, which rack is bolted to the telescoping arm 126. This causes arm 126 to be driven towards or away from the carriage assembly 82, depending on the direction of rotation of the Y axis motor 132. When the outer telescoping arm 126 is moved, it carries with it an idler gear 140 which is meshingly engaged between rack 142, which is attached to the inner telescoping arm 128, and rack 144 which is coupled to the carriage channel 130. For purposes of clarity, the illustration in FIG. 17 depicts only one half of the telescoping arrangement of the Y axis drive, but it will be understood that the Y axis motor 132 causes, through the action of another drive gear (not shown), both sets of telescoping arms 126 and 128 to be driven in a desired direction along the Y axis.

Figure 21:
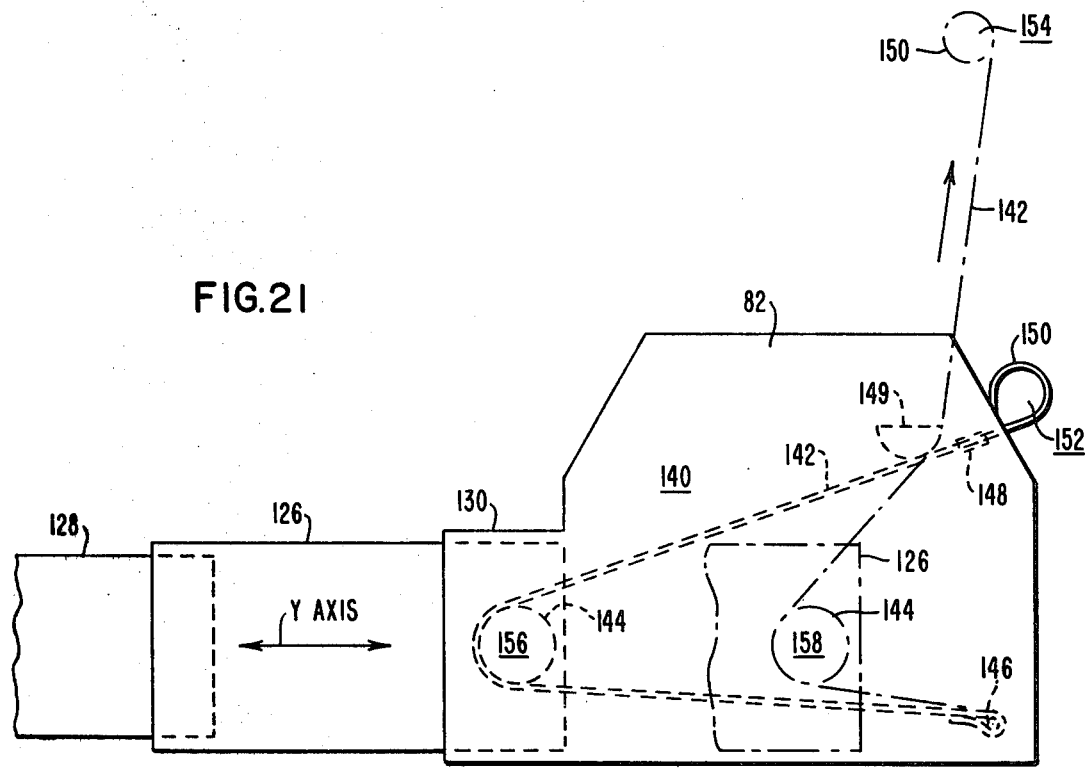
FIG. 21 is a plan view which representatively illustrates a manually operated emergency restruction system.

Movement of the manipulator arm 26 along the Y axis is required, in particular, to position the transducer array 28 within any one of the reactor vessel nozzles 38 for inspection thereof, as is shown in FIG. 9. In the event of total power failure or an inability to withdraw the transducer array 28 from within a nozzle 38, an emergency retraction assembly 140 is provided. As is depicted in FIG. 21, the emergency retraction assembly 140 includes a retraction cable 142 arranged within the carriage assembly 82 and extending therefrom to be looped about an idler pulley 144 which is rotatably mounted within and to the telescoping arm 126. Cable 142 also is guided by the half-pulley 149. One end of the retraction cable 142 is fixedly secured to the carriage assembly 82 by a clamp 146. The other end of the retraction cable 142 is formed into a ring 150 which is detachably secured to the carriage assembly 82 at an initial position 152 by a removable clamp 148. The ring 150 is mounted so as to be accessible from above.

The cable 212 can either be through-routed through the junction box 216 or terminated at a connector 225 provided for that purpose. In either event, the cable 212 is routed from junction box 216 into the larger cable or hose 214. Hose 214, with cable 212 disposed therein, includes a generally annular space 215 along its length to carry the pressurized air where needed. Cable 214 is clamped over nozzle 226 by clamp 228 to provide an air-tight fit between the air supply junction box 216 and the dual hose 214. From junction box 216, the hose 214 is routed to the underwater junction box 208. It is secured thereto by water-tight seals 230 and 232 at the points where it enters junction box 208. From the junction box 208, the hose 214 can be branched by internal connectors (not shown) to any one or more of the motors, resolvers, transducers, etc., used in the inspection apparatus 14. Further, since cable 214 can depart the junction box 208 carrying pressurized air, various motor and resolver housings can also be pressurized where desired.

Figure 24:
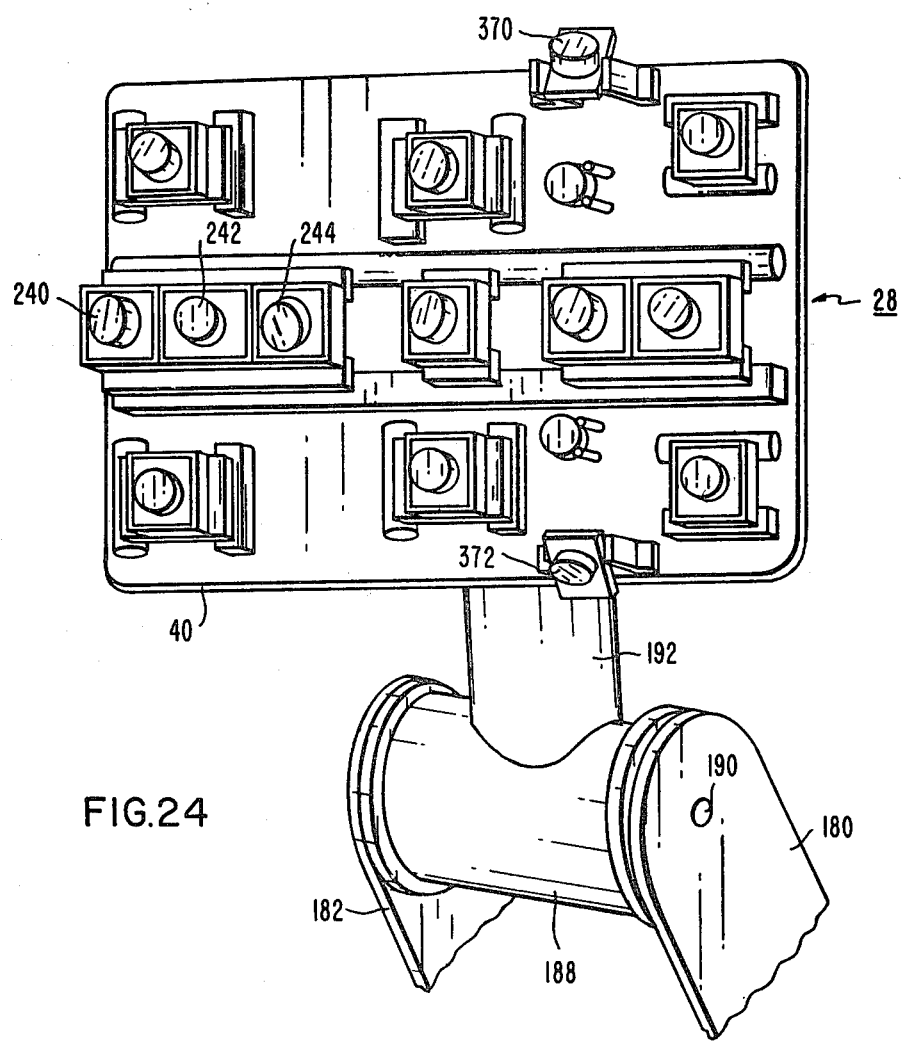
FIGS. 24 and 25 are isometric views of a transducer array carried by the manipulator arm.
Figure 25:
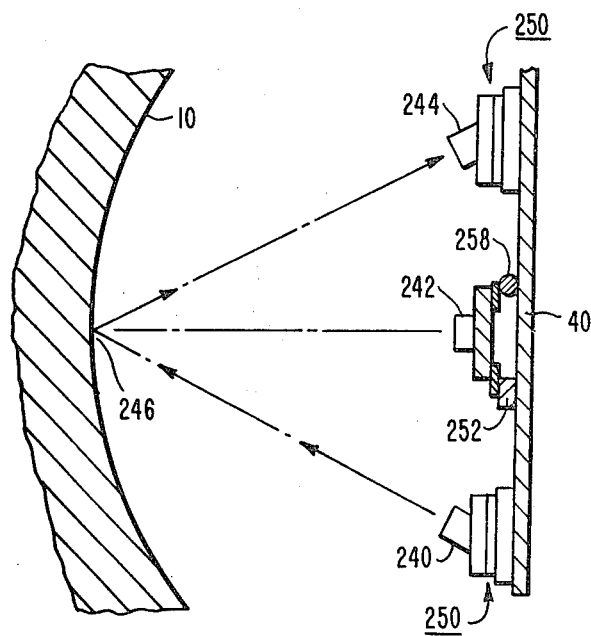

As previously noted, the transducer array 28 is employed as the examination means by which the integrity of the vessel welds 13 or any appropriate portion of the vessel 10 can be inspected. A typical plan view of the transducer array 28 disposed on the mounting plate 40 is shown in FIG. 24. It should be noted with respect to the individual transducers themselves, that they are grouped or arrayed in a manner which permits the manipulator arm 26 to optimally position the plate 40 so that the greatest inspection flexibility results. For example, the three transducers 240, 242, and 244 can be positioned, as illustrated in FIG. 25, to direct their ultrasonic beams to impinge at point 246 on the vessel 10. Transducer 242 can be oriented to impinge perpendicularly to the vessel wall at point 246 to verify the water path distance or to check for vessel flaws. Transducers 240 and 244 can be used to direct angled beams at point 246 which may be a weld point or material adjacent thereto. Further, transducers 240 and 244 may be coupled to pitch-catch or merely echo their respective beams.

Figure 26:
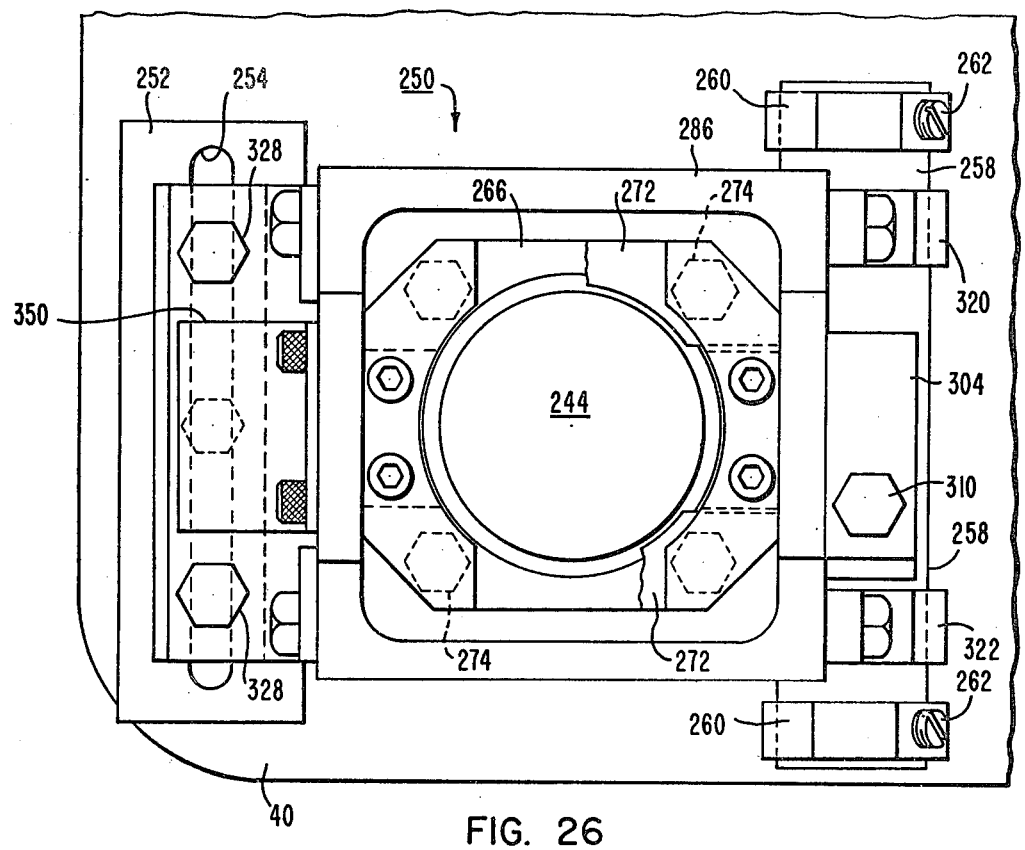
FIGS. 26 through 33 are plan or isometric views, some in partial section, illustrating the mounting assembly used for the transducers included in the array depicted in FIG. 24.
Figure 27:
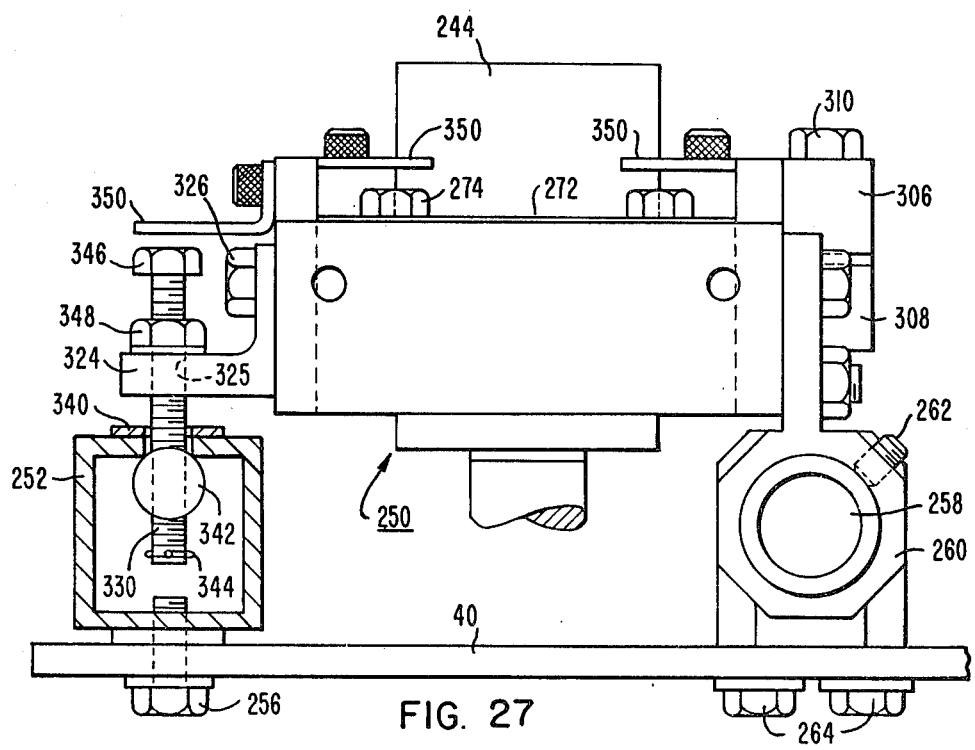

The individual transducers are secured to plate 40 by a transducer mounting assembly, generally designated 250, shown in FIGS. 26 and 27 in its normal orientation. The transducer mounting assembly includes a hollow, generally rectangularly shaped bar 252 having a slot 254 cut longitudinally therein. The bar 252 is bolted to the transducer plate 40 by bolts 256 one of which is shown in FIG. 27. A circular bar 258 is captured at either end thereof by holders 260 and fastened securely therein by set screws 262. The holders 260 are secured to the transducer plate 40 by bolts 264, also shown in FIG. 27, parallel to the spaced apart from bar 252.

A transducer 244 is held in a retaining block 266 having a circular bore 268 therein sized to accommodate the transducer 244. The top portion of bore 268 is countersunk or cut away to accept and support the flange 245 of transducer 244 in the circular shelf 270. Plates 272, which are fitted over and about the transducer flange 245 and secured to the top of retaining block 266 by bolts 274, tightly capture and retain the transducer 244 in the block 266. If necessary, the transducer 244 can be rotated in the retaining block by loosening the bolts 274. The retaining block 266 includes upstanding flanges 276 and 278 having circular bores 280 and 282 cut therethrough for respectively accepting a hinge pin 284 therein.

Figures 30, 31:
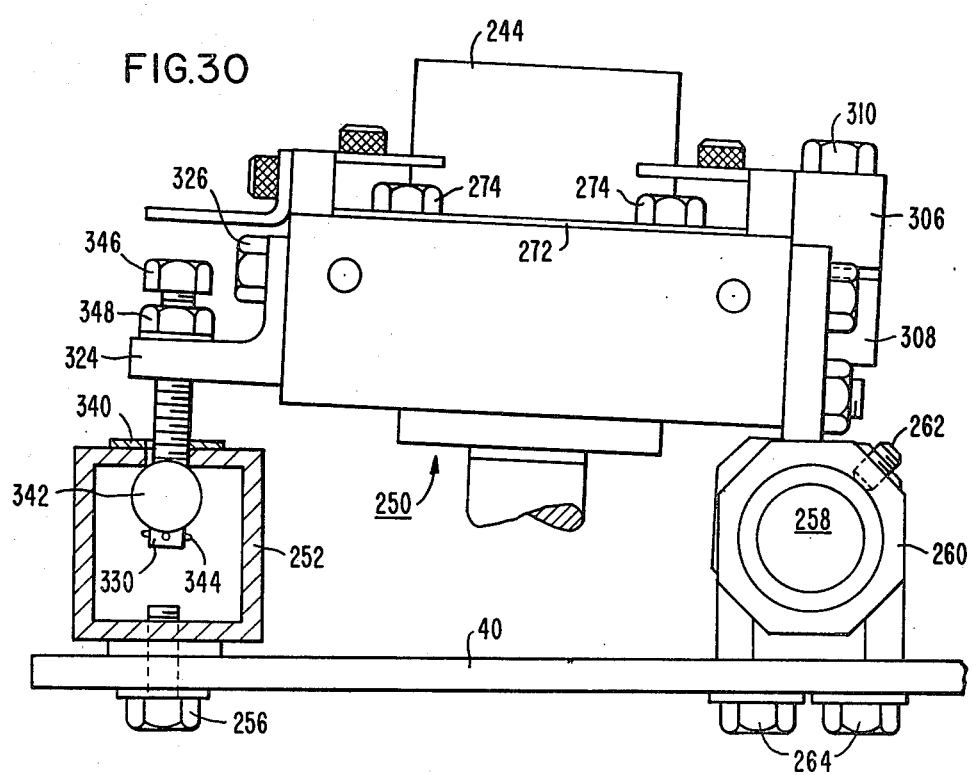
Figure 32:
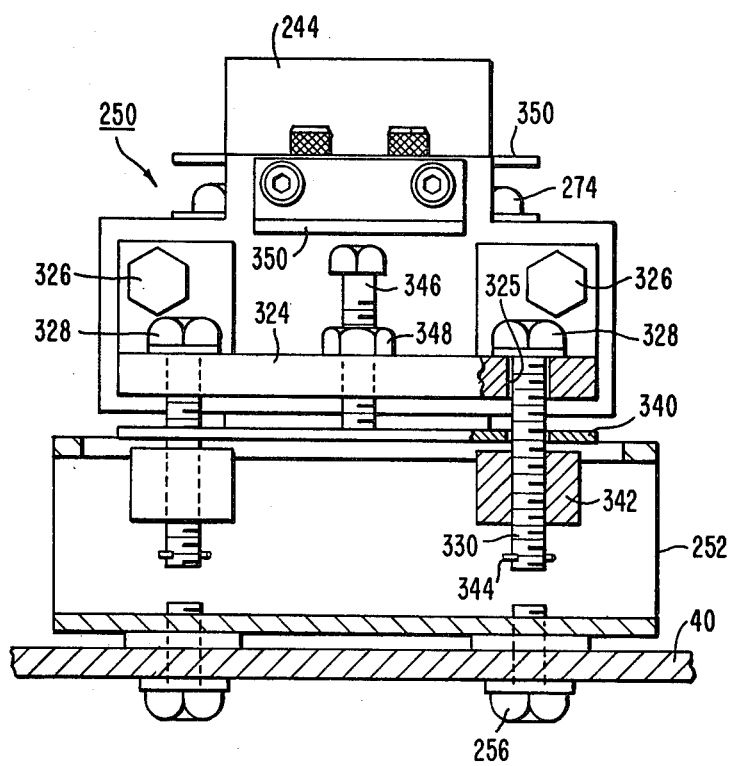
Figure 33:
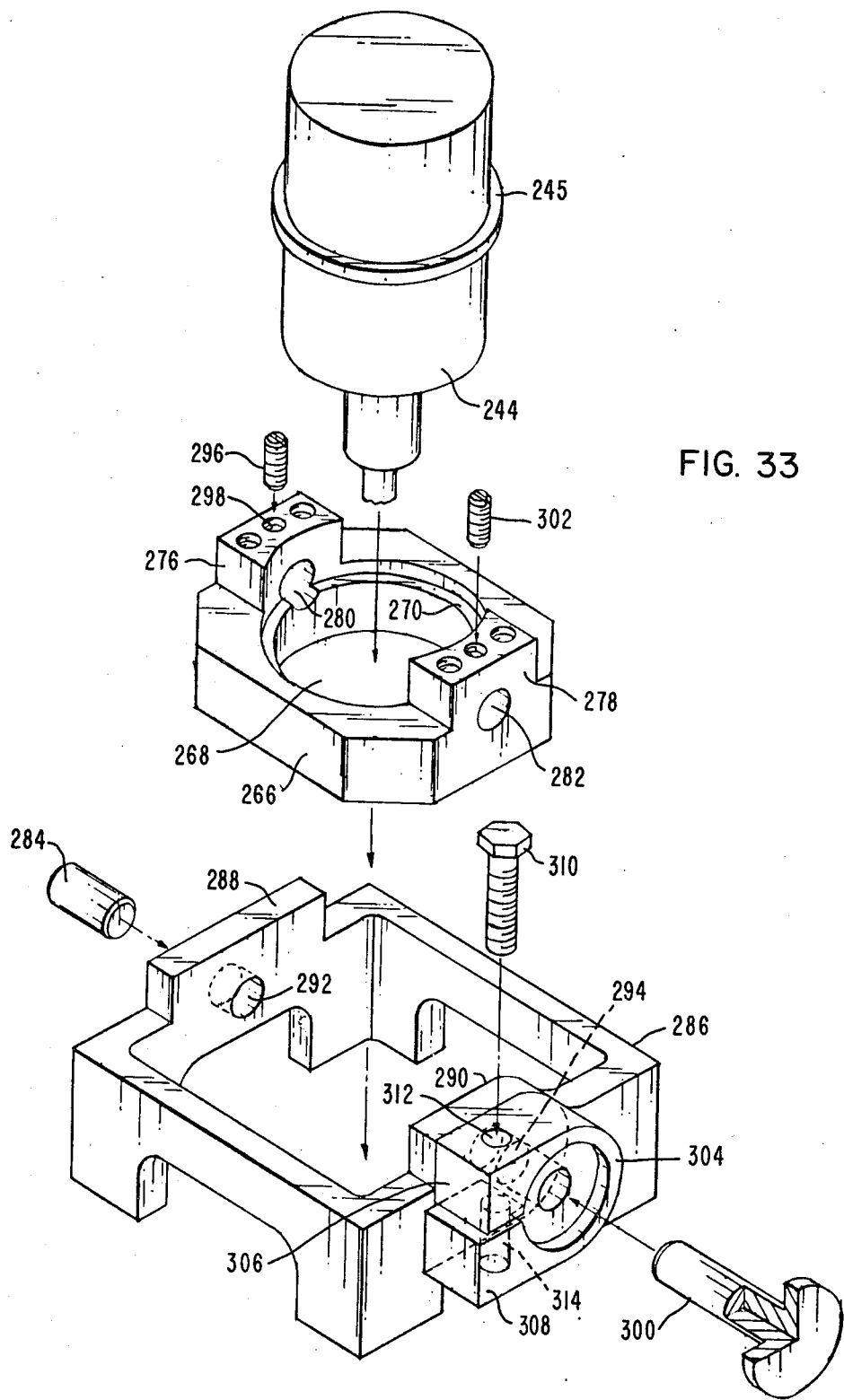

The retaining block 266 is, in turn, secured to a yoke 286 which also includes two upstanding flanges 288 and 290, each having a circular bore 292 and 294 cut respectively therein. The hinge pin 284 extends through the bores 280 and 292 to pivotally fasten one side each of the block 266 and the yoke 286 to each other. A set screw 296, extending from the top of flange 276 through a bore 298 therein is used to clamp the hinge pin 284 to the retaining block 266. The other end of hinge pin 284 remains free to rotate in bore 292 of flange 288. The other side of retaining block 266 is also pivotally secured to the yoke 286 by a hinge pin 300, which is "T" shaped in cross-section. The leg of hinge pin 300 extends through the bores 282 and 294 of flanges 278 and 290. It is secured within bore 282 and clamped to flange 278 by a set screw 302. The head portion of hinge pin 300 abuts the flange 290 and is captured by a "U" shaped clamp 304 which is bolted to flange 290. The leg portions 306 and 308 of clamp 304 are held together by a bolt 310 which is threaded through bores 312 and 314 cut respectively in leg portions 306 and 308. When the bolt 310 is tightened down, leg portions 306 and 308 are drawn tightly together about the head portion of hinge pin 300 preventing it from turning in clamp 304. When bolt 310 is loosened, however, the transducer 244 and the retaining block 266 can be pivoted about the hinge pins 284 and 300 A side view of a pivoted restraining block 266, with transducer 244 having been tilted forwardly, is shown in FIG. 31. An exploded isometric view of the transducer 244, restraining block 266 and yoke 286 coupling is illustrated in FIG. 33.

As shown in FIGS. 26 and 31, two circular sleeves 320 and 322 are fit over and slid along the circular bar 258 prior to its being clamped into the holders 260. The sleeves 320 and 322 are bolted to one side of the yoke 286 by bolts 321. An angle bracket 324 is secured to the other side of yoke 286 by bolts 326. The perpendicular portion of bracket 324 is bolted to the rectangular bar 252 by the end bolts 328. If bolts 328 are loosened, the yoke 286 and therefore the transducer 244 held therein can be moved transversely along the bars 252 and 258.

The bolts 328 pass through a bore 325 in the perpendicular portion of bracket 324 as illustrated in FIGS. 27, 30 and, most clearly, 32. After passing through the bore 325, the bolts extend through plate 340 and the slot 254 into the bar 252. The legs 330 of bolts 328 are threaded through the barrel nuts or pivots 342 and are pierced by cotter pins 344 at their terminal point ot prevent their being worked out of the barrel nuts 342. A centered bolt 346 is threaded through the perpendicular portion of bracket 324 and abuts the plate 340 which acts as a stop therefor. When a locknut 348 is loosened, the bolt 346 can be tightened down, increasing the distance between plate 340 and the bracket 324, thereby pivoting the yoke 286 about the circular bar 258. An example of a pivoted yoke 286 is shown in FIG. 30. When the bolt 346 is tightened, the barrel nuts 342 pivot in the slot 254 permitting the yoke 286 to move to its canted position. It should be noted that the end bolts 328 are not loosened to effect or aid in this pivoting motion of the yoke 286. A number of bolt head flanges 350 are used to cover and retain various bolts should they loosen and work out of engagement.

Figure 28:
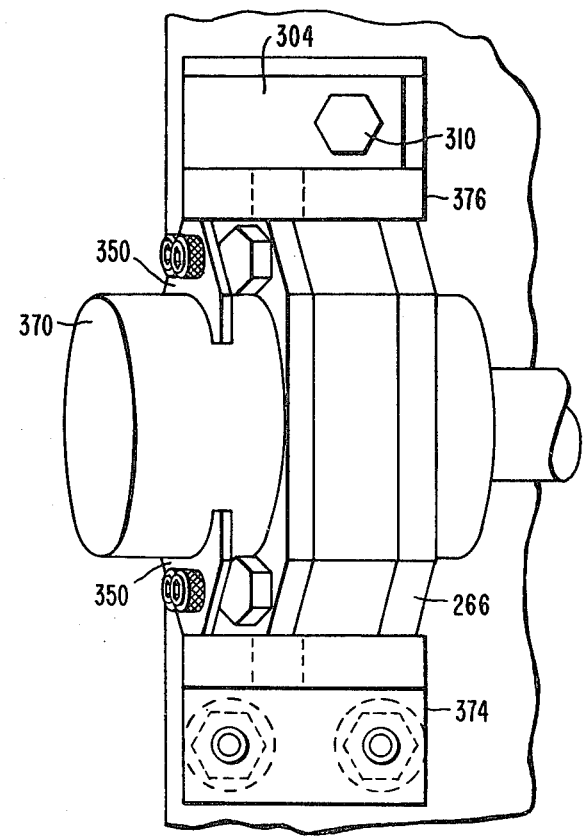
Figure 29:
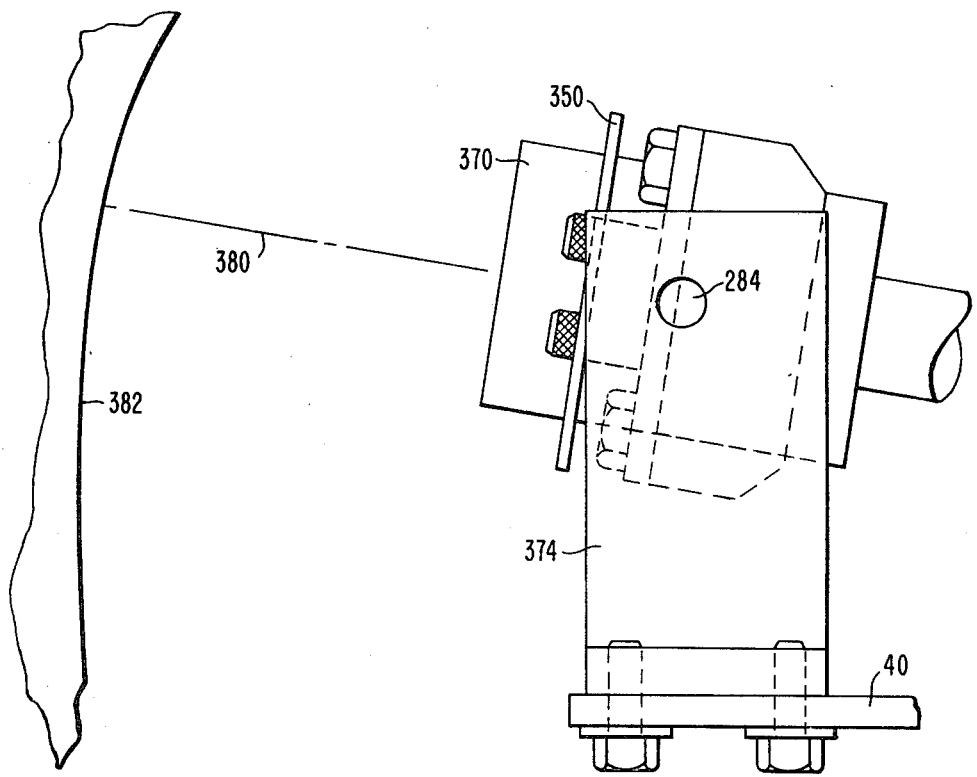

As the transducer array 28 is disposed about the vessel 10, particularly in or near one of the nozzles 38, it becomes difficult because of the curved vessel surfaces, to maintain one of the transducers perpendicular to the vessel wall and simultaneously insure proper clearances. For that reason, at least two transducers 370 and 372 are mounted on upstanding brackets 374 and 376 rather than on the bars 252 and 258. An example of this mounting arrangement is depicted in FIGS. 28 and 29. The restraining block 266 is removed from the yoke 286 and is bolted to the brackets 374 and 376. It is then pivoted at an appropriate angle by loosening bolt 310 of the "U" clamp 304 as previously described. In this case, however, clamp 304 is bolted to the block 266 rather than the yoke 286.

As shown in FIG. 29, the transducer beam 380 can be directed against the curved vessel wall 382, generally normal thereto, and the same transducer can be employed to receive the echo. Thus, the perpendicular distance between the transducer plate 40 and the vessel wall 382 can be continuously monitored. Utilizing such information, the manipulator arm 26 can be moved accordingly to prevent collisions. Thus, there has been described a versatile transducer mounting assembly which tightly retains a transducer therein, but which can be adjusted to permit translational, pivotal and rotary motion of the transducer relative to the mounting plate.

While the invention has been shown and described herein in considerable detail, such disclosure is to be considered as only illustrative or exemplary in character and not restrictive, as within the broad scope of the invention, modifications of or alternatives thereto may readily suggest themselves to persons skilled in this art.

We claim:

1. A positionally variable transducer mounting assembly for removably securing a transducer with respect to an array plate comprising:
    a rectangularly shaped bar having a longitudinal slot therein and bolted to said array plate;
    at least two holders secured to said array plate and spaced apart from and parallel to said rectangularly shaped bar;
    a circular bar held by said holders;
    a yoke rotatably mounted on said circular bar and slidably mounted on said rectangularly shaped bar for positioning said yoke with respect to said array plate;
    a retaining block having a circular bore therein and rotatably mounted on said yoke; and
    a transducer mounted in said retaining block for inspecting metal surfaces.

2. The mounting assembly according to claim 1 wherein said mounting assembly further comprises plates fitted over and about a flange on said transducer and secured to the top of said retaining block for securing said transducer in said retaining block.

* * * * *